(12) United States Patent
Eggert et al.

(10) Patent No.: US 9,406,244 B2
(45) Date of Patent: *Aug. 2, 2016

(54) INTERACTIVE EDUCATION SYSTEM FOR TEACHING PATIENT CARE

(71) Applicant: Gaumard Scientific Company, Inc., Miami, FL (US)

(72) Inventors: John S. Eggert, Miami, FL (US); Michael S. Eggert, Norfolk, VA (US); Alberto Rodriguez, Miami, FL (US)

(73) Assignee: Gaumard Scientific Company, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/684,148

(22) Filed: Apr. 10, 2015

(65) Prior Publication Data

US 2015/0221237 A1   Aug. 6, 2015

Related U.S. Application Data

(63) Continuation of application No. 14/223,687, filed on Mar. 24, 2014, now Pat. No. 9,004,922, which is a continuation of application No. 13/441,437, filed on Apr. 6, 2012, now Pat. No. 8,678,832, which is a (Continued)

(51) Int. Cl.
*G09B 23/38* (2006.01)
*G09B 23/28* (2006.01)
*G06F 19/00* (2011.01)

(52) U.S. Cl.
CPC .......... *G09B 23/281* (2013.01); *G06F 19/3437* (2013.01); *G09B 23/28* (2013.01)

(58) Field of Classification Search
USPC .......... 434/267, 268, 272, 273; 446/320, 330, 446/353
See application file for complete search history.

(56) References Cited

U.S. PATENT DOCUMENTS

| | | |
|---|---|---|
| 2,551,433 A | 5/1951 | Graves |
| 2,871,579 A | 2/1959 | Niiranen et al. |
| 3,520,071 A | 7/1970 | Abrahamson et al. |

(Continued)

FOREIGN PATENT DOCUMENTS

| | | |
|---|---|---|
| DE | 20221662 U1 | 11/2006 |
| GB | 2324902 | 4/1998 |

(Continued)

OTHER PUBLICATIONS

European Patent Office, International Search Report and Written Opinion dated Jul. 16, 2009, for Application No. PCT/US08/085471, 23 pages.

(Continued)

*Primary Examiner* — Kurt Fernstrom
(74) *Attorney, Agent, or Firm* — Haynes and Boone, LLP

(57) ABSTRACT

Interactive education systems for teaching patient care to a user are disclosed. In some instances a maternal simulator for teaching patient care to a user includes a body sized and shaped to simulate a pregnant woman; a birthing device positioned within a cavity of the body, the birthing device configured to interface with a fetal simulator and configured to translate and rotate the fetal simulator in a manner simulating a birthing sequence; and a distensible cervix coupled to the body, the distensible cervix defining a port that the fetal simulator moves through during the birthing sequence.

20 Claims, 22 Drawing Sheets

Related U.S. Application Data continuation of application No. 12/856,903, filed on Aug. 16, 2010, now Pat. No. 8,152,532, which is a continuation of application No. 11/538,306, filed on Oct. 3, 2006, now Pat. No. 7,811,090, which is a continuation-in-part of application No. 10/848,991, filed on May 19, 2004, now Pat. No. 7,114,954, which is a continuation of application No. 10/292,193, filed on Nov. 11, 2002, now Pat. No. 6,758,676, which is a continuation of application No. 09/684,030, filed on Oct. 6, 2000, now Pat. No. 6,503,087.

(56) References Cited

U.S. PATENT DOCUMENTS

| | | | |
|---|---|---|---|
| 3,557,471 | A | 1/1971 | Payne et al. |
| 3,641,703 | A | 2/1972 | Tepper et al. |
| 3,664,038 | A | 5/1972 | Searle et al. |
| 3,707,782 | A | 1/1973 | Alderson |
| 3,740,871 | A | 6/1973 | Berton et al. |
| 3,753,301 | A | 8/1973 | Daniel et al. |
| 3,797,130 | A | 3/1974 | Knapp et al. |
| 3,818,756 | A | 6/1974 | Barron et al. |
| 3,822,486 | A | 7/1974 | Knapp et al. |
| 3,824,709 | A | 7/1974 | Knapp et al. |
| 3,826,019 | A | 7/1974 | Knapp et al. |
| 3,866,350 | A | 2/1975 | Goldfarb et al. |
| 3,916,535 | A | 11/1975 | Hewson |
| 4,134,218 | A | 1/1979 | Adams et al. |
| 4,155,196 | A | 5/1979 | Bollinger et al. |
| 4,360,345 | A | 11/1982 | Hon |
| 4,395,235 | A | 7/1983 | Becker |
| 4,402,327 | A | 9/1983 | Lambert et al. |
| 4,430,893 | A | 2/1984 | Barkalow |
| 4,464,123 | A | 8/1984 | Glover et al. |
| 4,575,351 | A | 3/1986 | Gonzalez |
| 4,611,998 | A | 9/1986 | Ramamurthy |
| 4,691,556 | A | 9/1987 | Mellander et al. |
| 4,701,132 | A | 10/1987 | Groesch et al. |
| 4,726,772 | A | 2/1988 | Amplatz |
| 4,734,039 | A | 3/1988 | Thompson |
| 4,773,865 | A | 9/1988 | Baldwin |
| 4,797,104 | A | 1/1989 | Laerdal et al. |
| 4,820,236 | A | 4/1989 | Berliner et al. |
| 4,828,501 | A | 5/1989 | Ingenito et al. |
| 4,836,821 | A | 6/1989 | Raymond |
| 4,850,876 | A | 7/1989 | Lutaenko et al. |
| 4,867,685 | A | 9/1989 | Brush et al. |
| 4,907,973 | A | 3/1990 | Hon |
| 4,915,635 | A | 4/1990 | Ingenito et al. |
| 4,932,879 | A | 6/1990 | Ingenito et al. |
| 5,055,052 | A | 10/1991 | Johnsen |
| 5,083,962 | A | 1/1992 | Pracas |
| 5,100,329 | A | 3/1992 | Deesen et al. |
| 5,104,328 | A | 4/1992 | Lounsbury |
| 5,137,458 | A | 8/1992 | Ungs et al. |
| 5,195,896 | A | 3/1993 | Sweeney et al. |
| 5,259,765 | A | 11/1993 | Richards |
| 5,279,309 | A | 1/1994 | Taylor et al. |
| 5,295,835 | A | 3/1994 | Scheinberg et al. |
| 5,339,799 | A | 8/1994 | Kami et al. |
| 5,351,677 | A | 10/1994 | Kami et al. |
| 5,385,474 | A | 1/1995 | Brindle |
| 5,441,413 | A | 8/1995 | Kumar |
| 5,454,722 | A | 10/1995 | Holland et al. |
| 5,509,810 | A | 4/1996 | Schertz et al. |
| 5,513,992 | A | 5/1996 | Refait |
| 5,528,943 | A | 6/1996 | Smrcka et al. |
| 5,538,005 | A | 7/1996 | Harrison et al. |
| 5,540,592 | A | 7/1996 | Scheinberg et al. |
| 5,609,485 | A | 3/1997 | Bergman et al. |
| 5,620,326 | A | 4/1997 | Younker |
| 5,623,582 | A | 4/1997 | Rosenberg |
| 5,628,230 | A | 5/1997 | Flam |
| 5,704,791 | A | 1/1998 | Gillio |
| 5,755,577 | A | 5/1998 | Gillio |
| 5,769,640 | A | 6/1998 | Jacobus et al. |
| 5,799,282 | A | 8/1998 | Rakshit et al. |
| 5,800,179 | A | 9/1998 | Bailey |
| 5,828,197 | A | 10/1998 | Martin et al. |
| 5,853,292 | A | 12/1998 | Eggert et al. |
| 5,855,553 | A | 1/1999 | Tajima et al. |
| 5,882,206 | A | 3/1999 | Gillio |
| 5,941,757 | A | 8/1999 | Jurmain et al. |
| 6,022,263 | A | 2/2000 | Liu et al. |
| 6,024,576 | A | 2/2000 | Bivirt et al. |
| 6,050,826 | A | 4/2000 | Christianson et al. |
| 6,088,017 | A | 7/2000 | Tremblay et al. |
| 6,088,020 | A | 7/2000 | Mor |
| 6,089,873 | A | 7/2000 | Jurmain et al. |
| 6,091,981 | A | 7/2000 | Cundari et al. |
| 6,106,301 | A | 8/2000 | Merril |
| 6,113,395 | A | 9/2000 | Hon |
| 6,117,078 | A | 9/2000 | Lysyanskyt et al. |
| 6,193,519 | B1 | 2/2001 | Eggert et al. |
| 6,219,032 | B1 | 4/2001 | Rosenberg et al. |
| 6,220,866 | B1 | 4/2001 | Amend et al. |
| 6,230,574 | B1 | 5/2001 | Rider et al. |
| 6,234,804 | B1 | 5/2001 | Yong |
| 6,238,215 | B1 | 5/2001 | Jurmain et al. |
| 6,267,599 | B1 | 7/2001 | Bailey |
| 6,296,490 | B1 | 10/2001 | Bowden |
| 6,306,107 | B1 | 10/2001 | Myklebust et al. |
| 6,375,471 | B1 | 4/2002 | Wendlandt et al. |
| 6,428,321 | B1 | 8/2002 | Jurmain et al. |
| 6,443,735 | B1 | 9/2002 | Eggert et al. |
| 6,470,302 | B1 | 10/2002 | Cunningham et al. |
| 6,503,087 | B1 | 1/2003 | Eggert et al. |
| 6,527,558 | B1 | 3/2003 | Eggert et al. |
| 6,544,041 | B1 | 4/2003 | Damadian |
| 6,547,782 | B1 | 4/2003 | Taylor |
| 6,575,757 | B1 | 6/2003 | Leight et al. |
| 6,638,073 | B1 | 10/2003 | Kazimirov et al. |
| 6,669,483 | B1 | 12/2003 | Leight et al. |
| 6,705,871 | B1 | 3/2004 | Bevirt et al. |
| 6,749,433 | B2 | 6/2004 | Kassi et al. |
| 6,758,676 | B2 | 7/2004 | Eggert et al. |
| 6,850,222 | B1 | 2/2005 | Rosenberg |
| 6,857,878 | B1 | 2/2005 | Chosack et al. |
| 6,863,536 | B1 | 3/2005 | Fisher et al. |
| 6,923,081 | B2 | 8/2005 | Krstic |
| 6,929,481 | B1 | 8/2005 | Alexander et al. |
| 6,946,812 | B1 | 9/2005 | Martin et al. |
| 6,997,718 | B1 | 2/2006 | Boettcher et al. |
| 7,114,954 | B2 | 10/2006 | Eggert et al. |
| 7,192,284 | B2 | 3/2007 | Eggert et al. |
| 7,465,168 | B2 | 12/2008 | Allen et al. |
| 2004/0110117 | A1 | 6/2004 | Van Oostrom et al. |
| 2007/0122785 | A1 | 5/2007 | Eggert et al. |
| 2007/0172804 | A1 | 7/2007 | Allen et al. |
| 2008/0131855 | A1 | 6/2008 | Eggert et al. |
| 2008/0138778 | A1 | 6/2008 | Eggert et al. |
| 2008/0138779 | A1 | 6/2008 | Eggert et al. |
| 2008/0138780 | A1 | 6/2008 | Eggert et al. |
| 2009/0148822 | A1 | 6/2009 | Eggert et al. |

FOREIGN PATENT DOCUMENTS

| | | |
|---|---|---|
| JP | 5528028 | 2/1980 |
| JP | 63011018 | 2/1985 |
| JP | 60030769 | 3/1985 |
| JP | 63060180 | 4/1988 |
| JP | 04008447 | 1/1992 |
| WO | WO-96/16389 | 5/1996 |

(56) References Cited

FOREIGN PATENT DOCUMENTS

| WO | WO-02/01536 | 1/2002 |
| WO | WO-02/29765 | 4/2002 |
| WO | WO-03/041034 | 5/2003 |
| WO | WO-2005/032327 | 4/2005 |
| WO | WO-2005/053508 | 6/2005 |
| WO | WO-2005/122111 | 12/2005 |
| WO | WO-2008/042931 | 4/2008 |
| WO | WO-2009/076145 | 12/2008 |

OTHER PUBLICATIONS

European Patent Office, International Search Report dated Feb. 28, 2008, for Application No. PCT/US07/080252, 3 pages.
Brett, P. N., "A Technique for Measuring Contact Force Distribution in Minimally Invasive Surgical Procedures," National Library of Medicine MEDLINE Database, 1997, 1 page.
Allen, R. H., "Simulating Birth to Investigate Clinician-Applied Loads on Newborns," National Library of Medicine MEDLINE Database, Jul. 1995, 1 page.
Crofts, Joanna F., et al., "Training for Shoulder Dystocia," Obstetrics & Gynecology, vol. 108, No. 6, Dec. 2006, p. 1477-1485.
University of Miami, Division of Research in Medical Education, "Harvey"—The Cardiology Patient Simulator, 5 pages.
Medical Educational Technology, Human Patient Simulator, 1996, 9 pages.
Loral Data Physiology, Pharmacology & Technology Together in the Human Patient Simulator, Aug. 1994, 8 pages.
Loral Data Education Curriculum Example Scenario, Human Patient Simulator, Jul. 1994, 8 pages.
Loral Data Physiology, Pharmacology & Technology Together in the Human Patient Simulator, Mar. 1994, 3 pages.
Promotional Literature, Advanced Cardiac Life Support Learning System, Ambu MegaCode Trainer System and Ambu Defib Training Manikin, May 1996, 9 pages.
Promotional Literature, Human Patient Simulator, 1994, Loral Data Systems, 4 pages.
Medical Testing Takes Leap into Future, newspaper article, Nov. 8, 1994, 2 pages.
Nasco Health Care Educational Materials. 1996-1997 catalogue, 23 pages.
Easy ACLS Quick reference Chart 2, Advanced Cardiac Life Support Preparation Manual, 1995, 11 pages.
Gaumard Scientific 95-96 Catalogue, 2 pages.
Human Patient Simulator, Clinical Features Summary, Medical Education Technology, 2002-2003, 11 pages.
Putting It All Together, Laerdal ALS Trainer Product Information, 2 pages.
Helping Save Lives, Laerdal Catalogue, 1992, 10 pages.
Armstrong 1996, Anesthesia Emergency Code Team, METI, EMS Respiratory ICU/CCU, 15 pages.
METI, The Biggest Smallest Innovation, Pediasim Simulation Technology, 1999, 4 pages.
www.laedal.com, Early Defibrillation Products, Laerdal AED Trainer and Laerdal Early Defibrillation Training Manikins, Nov. 16, 1998, 2 pages.
METI, Practice is the Best Teacher Brochure, 1997, 4 pages.
Gaumard Scientific 2002-2003 Catalogue, 88 pages.
Noelle Maternal and Neonatal Birthing Simulator Product Promotional Information, 2002, 16 pages.
Lifesaving Products for Today's Good Samaritans, Laerdal Catalogue, 2003, 7 pages.
International Search Report and Written Opinion for PCT/US2004/39409, dated Oct. 24, 2005, 9 pages.
Japanese Patent Office, Office Action dated May 18, 2005, Application No. 2002/533260, 7 pages.
European Patent Office, Office Action dated Nov. 22, 2005, Application No. 01977908.1, 4 pages.
Japanese Patent Office, Office Action dated Dec. 8, 2009, Application No. 2009-143583, 5 pages.
Loral Data Systems Delivers Human patient Simulator, news release, Aug. 1994, 1 page.
European Office Action received in Euroopean Application No. 08860019.2-1958, dated Jul. 8, 2014, 5 pages.

Fig. 16

INTERACTIVE EDUCATION SYSTEM FOR TEACHING PATIENT CARE

CROSS-REFERENCE TO RELATED APPLICATION

This application is a continuation of U.S. application Ser. No. 14/223,687 filed Mar. 24, 2014, now U.S. Pat. No. 9,004, 922, which is a continuation of U.S. application Ser. No. 13/441,437, now U.S. Pat. No. 8,678,832, filed Apr. 6, 2012, which is continuation of U.S. application Ser. No. 12/856, 903, now U.S. Pat. No. 8,152,532, filed Aug. 16, 2010, which is a continuation of U.S. application Ser. No. 11/538,306, now U.S. Pat. No. 7,811,090, filed on Oct. 3, 2006, which is a continuation-in-part of U.S. Ser. No. 10/848,991, now U.S. Pat. No. 7,114,954, filed on May 19, 2004, which is a continuation of U.S. Ser. No. 10/292,193, now U.S. Pat. No. 6,758,676, filed on Nov. 11, 2002, which is a continuation of U.S. Ser. No. 09/684,030, now U.S. Pat. No. 6,503,087, filed on Oct. 6, 2000. The entire disclosures of the foregoing applications are hereby incorporated by reference. Also incorporated by reference is the entire disclosure of U.S. Ser. No. 10/721,307, now U.S. Pat. No. 7,192,284, filed on Nov. 25, 2003, which is a continuation-in-part of U.S. Ser. No. 10/292, 193, now U.S. Pat. No. 6,758,676, filed on Nov. 11, 2002.

BACKGROUND

The present embodiment relates generally to an interactive education system for teaching patient care, and more particularly to such a system having virtual instruments for use with a child birthing patient simulator in conducting patient care activity.

While it is desirable to train students in patient care protocols before allowing contact with real patients, textbooks and flash cards lack the important benefit to students attained from "hands-on" practice. Thus, patient care education has often been taught using medical instruments to perform patient care activity on a simulator, such as a manikin. However, one disadvantage of such a system is that medical instruments are often prohibitively expensive, and consequently, many users must settle for using a smaller variety of instruments, even at the cost of a less comprehensive educational experience. One solution to the foregoing problem is using a set of relatively inexpensive, simulated medical instruments ("virtual" instruments), as taught in U.S. Pat. No. 5,853,292, the entire disclosure of which is hereby incorporated by reference. Another solution is for the simulators to be compatible with real medical instruments.

Another problem in patient care education is that the patient simulators used for teaching a user are generally passive. For example, in a child birthing simulation, a user must position the simulated fetus in a simulated maternal pelvis, move it down the birth canal, birth the fetus's head, rotate the fetus approximately ninety degrees to birth the shoulders, and finally, pull out the fetus, now referred to as a neonate. While replicating the sequence of events in a real delivery, the lack of verisimilitude resulting from physical manipulation of the fetus by the user undermines an appreciation for the difficulties of providing patient care. In a real delivery, the fetus is inaccessible, and most activity is obscured from view, and thus prior systems fail to address the most challenging conditions of providing patient care during child birthing. Moreover, prior systems fail to simulate cervical dilation as the fetus moves down the birth canal, thus failing to allow a student to assess the stage of delivery or construct a chart of cervical dilation versus time to assess the progress of delivery ("Partograph").

Further, another problem in patient care education is that often the systems are too bulky and require too many wired connections to other components, which prevents easy transportation of the simulator to other locations. Often systems that claim to be "portable" require moving the numerous attached components, such as compressors and power supplies, for the simulator to be fully-functional. A solution to this problem is to make the simulators fully-functional, self-contained simulators that communicate with external devices wirelessly. Therefore, what is needed is a system for an interactive education system for use in conducting patient care training sessions that includes a more realistic simulated patient(s).

SUMMARY

The present embodiment provides an interactive education system for teaching patient care to a user. The system includes a maternal simulator, a fetal simulator designed to be used both in conjunction with the maternal simulator and separate from the maternal simulator, and neonatal simulator designed to replace the fetal simulator in post-birth simulations. In some embodiments, the system includes simulators that are completely tetherless. That is, the simulator is functional without the need for wired connections to other external instruments, devices, or power supplies. In such embodiments, the simulator may communicate with other devices or instruments wirelessly.

BRIEF DESCRIPTION OF THE DRAWINGS

FIGS. 12-16 are screen display views generated by a program according to one embodiment of the present system.

DETAILED DESCRIPTION

Figure 1A:
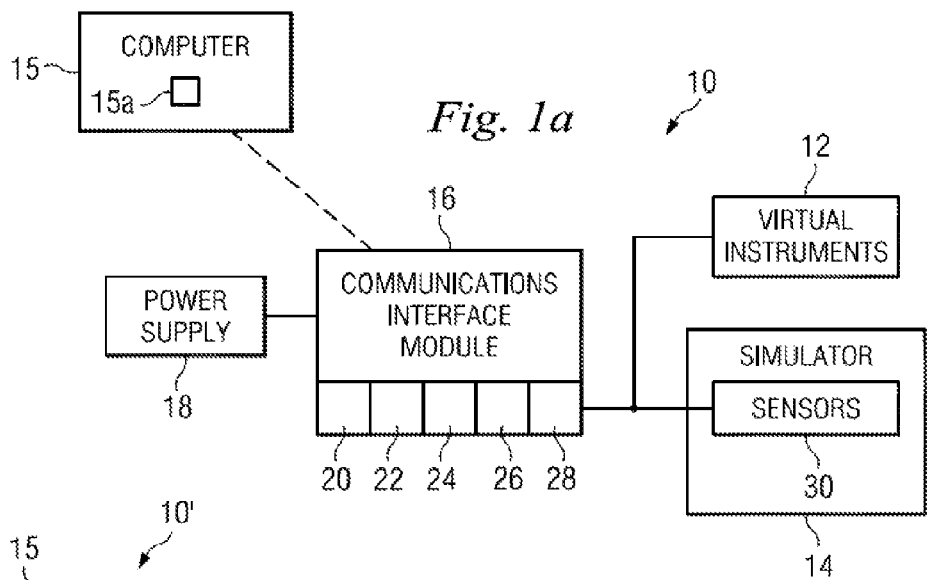
FIG. 1a is a schematic view of an illustrative embodiment of an interactive education system.

Referring to FIG. 1a, the reference numeral 10 refers, in general, to an interactive education system for teaching patient care protocols to a user. The system 10 comprises a set of virtual instruments 12 used to simulate medical instruments, and a simulator 14 used to simulate at least one patient for receiving patient care activity from the user. The virtual instruments 12 are tangible objects, and look, feel, and operate like real medical devices in conjunction with the simulator 14, which is understood to encompass a variety of forms, including a fully articulating and adult-sized manikin, as well as a fetus, a neonate, a child, a youth, or portion of a manikin, such as the arm, torso, head, or pelvic region.

Patient care activity received by the simulator 14 from the user, or users, is sensed in a manner to be described, and in response to the activity, the system 10 provides feedback to the user. It is understood that feedback may comprise any audio, visual, or tactile response. A computer 15 having a program 15a is optionally connected to the system 10, for reasons to be described.

Figure 1B:
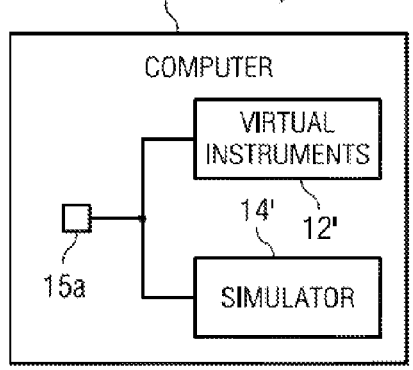
FIG. 1b is a schematic view of an interactive education system according to another embodiment.

Referring to FIG. 1b, a system 10' comprises the computer 15 and the program 15a, wherein a software-generated set of virtual instruments 12' and a software-generated simulator 14' is provided. Thus, the patient care activity performed by the user comprises manipulating an icon relating to a selected software-generated virtual instrument 12' to provide patient care to the software-generated simulator 14'. In this embodiment, the program 15a uses conventional means, such as clicking a mouse or voice-activated software, to monitor activity by the user, and provides feedback in response, as will be described.

Returning to FIG. 1a, the system 10 further comprises a communications interface module ("CIM") 16, which receives operating power from a conventional power source 18, and contains a microcontroller ("PIC") 20. Microcontrollers are available from many vendors, such as Microchip Technology, Inc. (Chandler, Ariz.), and are then customized. As will be described, the PIC 20 receives input signals from the user's activity, and is programmed to respond in a certain manner to provide feedback to the user. For example, to provide audio feedback, the CIM 16 additionally includes an audio chip 22 which is responsive to the PIC 20 for causing a speaker 24 to produce realistic patient sounds, for example, heart, lung, blood pressure (Korotkoff), intestinal, fetal, and the like. A control 26 is included in the CIM 16 for adjusting the volume of the speaker 24.

Alternatively, depending on the complexity of the desired feedback, the CIM 16 may be connected to the computer 15 and program 15a. In one example of feedback, the program 15a could be used to provide a vast library, for example, of ultrasound profiles, or fetal distress monitor traces. Feedback could also be of body sounds, generated by the program 15a, and played through speakers of the computer.

The CIM 16 has a plurality of ports, collectively 28, for receiving input signals occasioned by interaction between the virtual instruments 12 and sensors 30 disposed on the simulator 14, resulting from the user's patient care activity. It is understood that there may be more than one PIC 20, and more than one CIM 16, to manage the input signals thus created.

Figure 2:
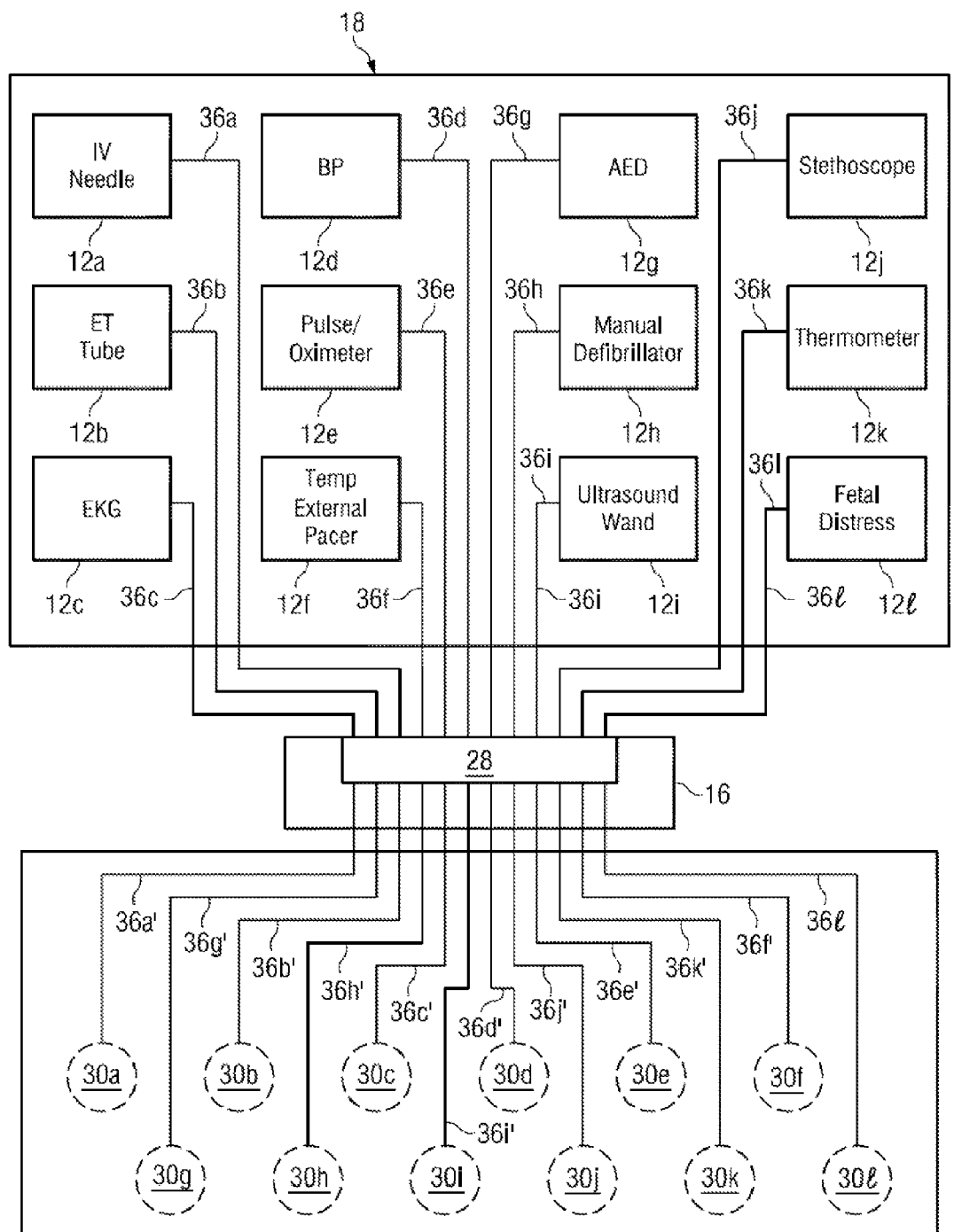
FIG. 2 is a schematic view of the interaction between a set of virtual instruments and a patient simulator.

The virtual instruments 12 comprise patient care devices, for example, as shown in FIG. 2, at least one IV needle, an endotracheal (ET) tube, an electrocardiogram (ECG or EKG) monitor, a blood pressure (BP) cuff, a pulse oximeter cuff, a temporary external pacer, an automatic external defibrillator (AED), a manual defibrillator, an ultrasound wand, a virtual stethoscope, a thermometer, and a fetal distress monitor, respectively 12a-l. Such virtual instruments look and operate like real medical devices. Of course, other virtual instruments are contemplated, as is the use of relatively inexpensive medical devices, such as a conventional stethoscope, a vacuum extractor, catheters, trays, IV stands, and the like.

Referring to FIG. 2, the IV needle 12a has a selectable group of specific drugs and dosages, and in one embodiment is part of a medication tray with an assortment of labeled syringes for dispensing the drugs to the simulator 14, with the effects of administration controlled by the program 15a. The ET tube 12b is used in simulated patient airway management, and placed in a tracheal airway of the simulator 14. The EKG monitor 12c comprises a 3, 5, or 12 lead system, including a real-time trace monitor and R-wave sonic markers, and a plurality of color-coded patches for attachment to a torso of the simulator 14. The BP cuff 12d attaches to the simulator 14, for example, around an arm. The pulse oximeter finger cuff 12e attaches to the simulator 14, for example, around a finger. The temporary external pacer 12f has a plurality of anterior and posterior pacer pads for attachment to the torso of the simulator 14. The pacer 12f has controls for pacer rate and current, and exhibits rhythm pacing, cap time, and loss of cap time, all of which is controlled by the program 15a. The automatic external defibrillator (AED) 12g has a plurality of apex and sternum AED pads for attachment to the torso of the simulator 14. Upon selecting a software-generated shock button produced by the program 15a, the system 10 simulates defibrillation shock, with the resultant conditions controlled by the program 15a. The manual defibrillator 12h has a plurality of apex and sternum defibrillator paddles for contacting the torso of the simulator 14. Upon selecting a software-generated shock button, or alternatively by using a dual shock buttons associated with manual defibrillator 12h, the system 10 simulates defibrillation shock, with the resultant conditions controlled by the program 15a.

Still referring to FIG. 2, the ultrasound wand 12i interacts with the simulator 14, such that when the wand 30i is brought within a predetermined proximity of a predetermined anatomical area of the simulator, the CIM 16 detects the interaction and the program 15a supplies an ultrasound profile taken from a library of ultrasound images and or sounds. The program 15a may select between normal and abnormal profiles, requiring the user to interpret the profile and respond accordingly. The virtual stethoscope 12*j* interacts with the simulator 14, such that when the stethoscope 12*j* is brought within a predetermined proximity of a predetermined anatomical area of the simulator, the CIM 16 detects the interaction and feedback is supplied to the user, as will be explained below, with FIGS. 3*a*-*b*. The thermometer 12*k* interacts with the simulator 14, such that when the thermometer 12*k* is brought within a predetermined proximity of a predetermined anatomical area of the simulator, the CIM detects the interaction and the program 15*a* supplies a temperature reading. The fetal distress monitor 12*l* (tocodynomometer) attaches to a portion of the simulator 14, and upon attachment, the program 15*a* supplies a heart rate reading for a simulated fetus.

Each instrument has a corresponding sensor 30*a*-*l*, as indicated by lines, collectively 36. Unless otherwise indicated, the lines 36 are schematic, and merely illustrate that the virtual instruments 12 and the sensors 30 are functionally connected to each other for providing an interaction created by the user's patient care activity, the interaction being reported as an input signal to the CIM 16. It is understood that the sharing of such physical lines among instruments 12, or sensors 30, is contemplated as well.

Interaction between the virtual instruments 12 and the sensors 30 may be electrical, optical, pressure differential, tactile, temperature-controlled, or wireless. Generally speaking, an electrical interaction (which would also provide the input signal) could be created via a virtual instrument 12 having one node and a sensor 30 with another node, both of which are physically connected to the CIM 16, or by a virtual instrument with two nodes and a sensor formed of conductive material, or vice versa, only one of which may be physically connected to the CIM 16. For example, the IV needle 12*a* corresponds with a portion of the simulator 14 capable of accepting medications, such as the antecubital region of an arm, which may have a sensor 30*a* comprising an insulator sandwiched between two layers of conductive material having an appropriate thickness and weave density for permitting the needle 12*a* to pass through the cloth at a low acute angle (e.g., 20). The conductive layers of the sensor 30*a* are electrically coupled to the CIM 16 via line 36*a*', such that when the needle 12*a* is correctly passed through the two conductive layers, simulating cannulation of a vein of the simulator 14, a circuit is completed between the layers and sensed by the CIM 16.

In another example of a method of sensing interaction, the ET tube 12*b* is used in simulated patient airway management, the simulator 14 having a head, eyes, a nose, a mouth, and a realistic airway capable of accepting conventional airway adjuncts, with the airway configuration adjustable to display a large tongue, an obstructed pharynx, or closed vocal cords, to increase the difficulty of the patient care activity. In order to confirm proper placement in the tracheal airway of the simulator 14, an optical sensor 30*b* is mounted in the wall of the trachea of the simulator 14 and connected to the CIM 16 via line 36*b*'. Correct placement of the ET tube 12*b* in the trachea is confirmed when the tip of the ET tube interrupts the beam of the optical sensor 30*b*. The sensor 30*b* may also be used to determine whether a fluid has passed.

The virtual stethoscope 12*j* provides an example of a wireless method of sensing interaction. At least one sensor 30*j* is placed at an anatomical location on the simulator 14 where specific heart, lung (including airway), Korotkoff, fetal, or other sounds are normally heard. The sensor 30*j* provides at least one signal which is identified by the stethoscope 12*j*, thereby directing an integrated sound circuit to play a sound to the user appropriate for the anatomical location of the sensor on the simulator 14. It is understood that the sound circuit has a stored library of body sounds corresponding to the location of the selected sensor 30*j*, and that the sensor 30*j* is illustrative of any number of similar sensors.

Figure 3B:
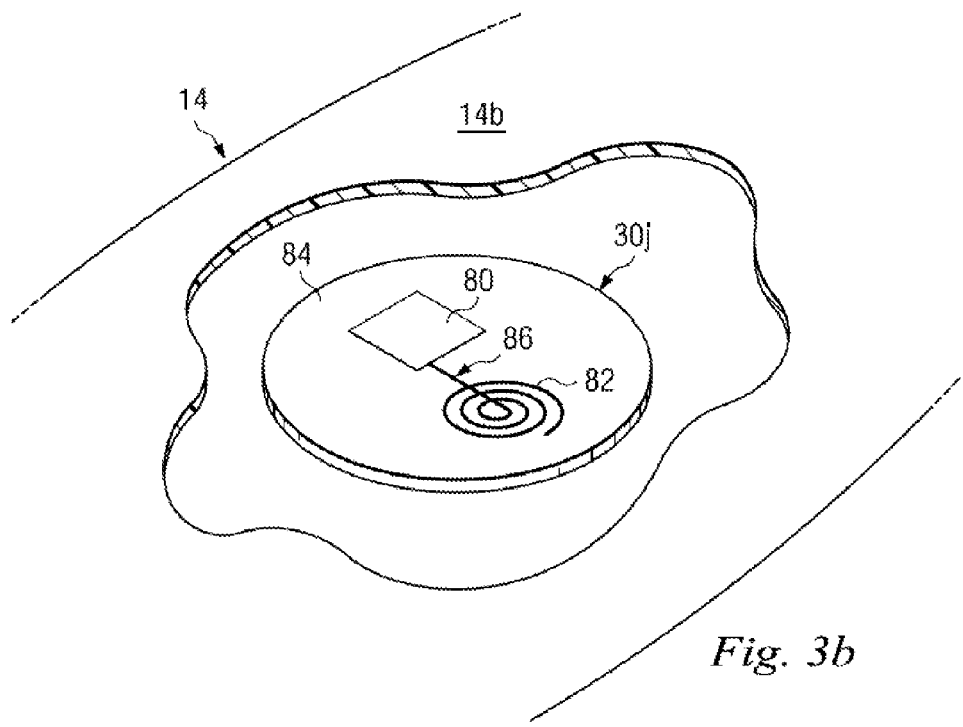
FIG. 3b is a perspective view with a cutaway of a sensor.
Figure 3A:
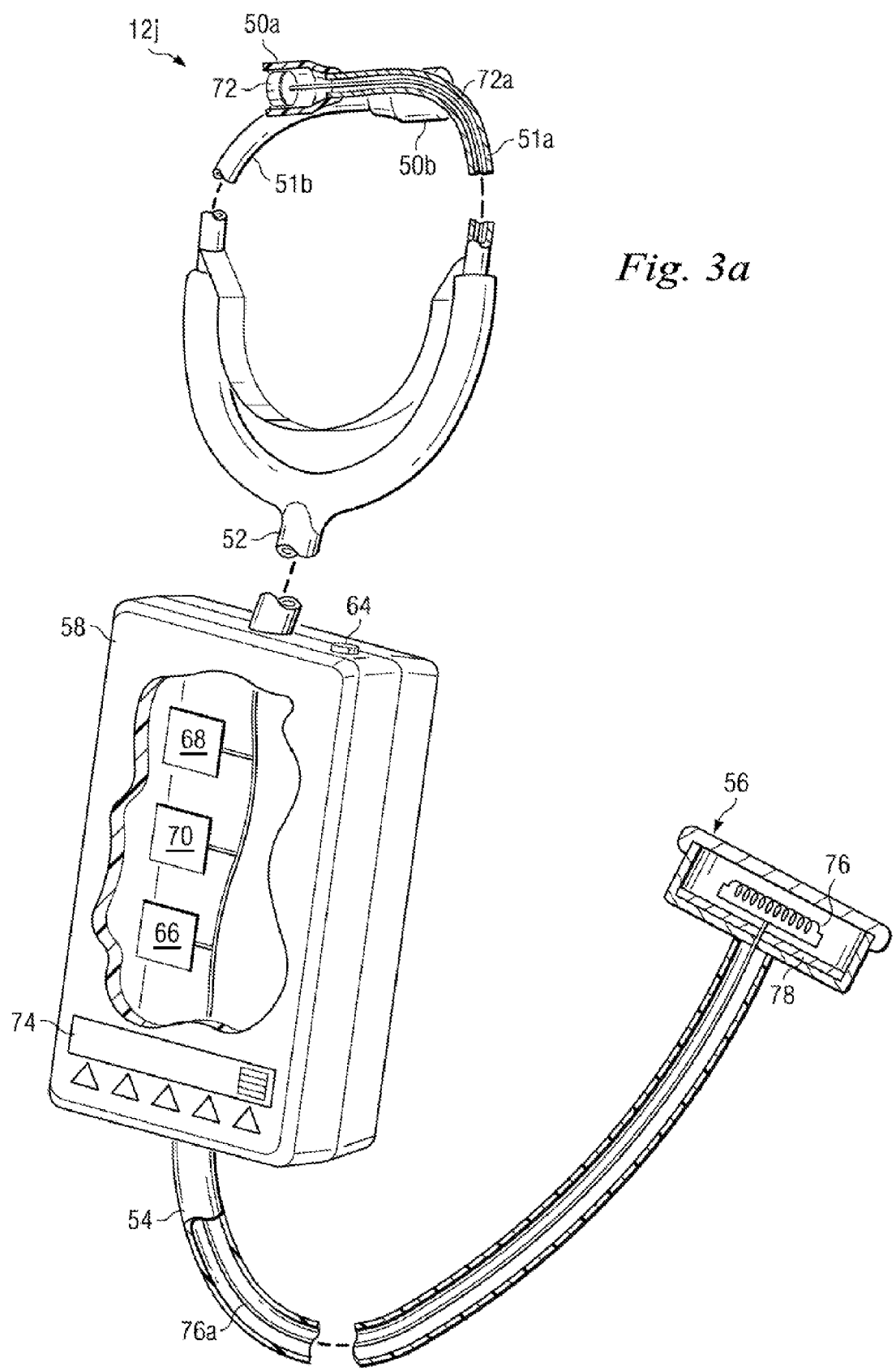
FIG. 3a is a perspective view with a cutaway of a virtual instrument.

Referring to FIG. 3*a*, in some respects, the appearance of the stethoscope 12*j* resembles a standard stethoscope, having earpieces 50*a*-*b* for hearing sounds, and being connected to extenders 51*a*-*b*, which are joined to a bifurcated ear tube 52. Similarly, the stethoscope further comprises a bell tube 54, and a bell 56, preferably made of nonferrous material. However, unlike conventional stethoscopes, an electronic control box 58 is disposed between the ear tube 52 and the bell tube 54. The control box 58 is understood to be an appropriately developed CIM 16, physically integrated into the virtual instrument 12*j*, thus simplifying the system 10. A jack 64 is provided on the control box 58 for output to an external speaker (not depicted), so that other users may hear the sounds heard in the earpieces 50*a*-*b*. This not only increases the number of users who benefit from the patient care activity, but allows an instructor to test the user's ability, and correct the user's technique if required. The control box 58 retains a small power source 66, such as a battery, an acquisition circuit 68 and a sound circuit 70 (see copending U.S. application Ser. No. 09/640,700, filed Aug. 17, 2000, for circuit diagrams) for directing a small speaker 72, such as is available from ADDAX Sound Company (Northbrook, Ill.), to play a predetermined sound. The speaker 72 is disposed in the earpiece 50*a*, and connected to the control box 58 via a wire 72*a*, allowing the user to hear the sounds produced by the sound circuit 70. It is understood that a second, substantially identical speaker may be disposed in the opposite earpiece 50*b*, and also connected to the control box 58. In an alternative embodiment, the speaker 72 may be disposed in the control box 58, and sounds transmitted via conventional ear tubes to the ear pieces. The sound circuit 70 is also connected to the jack 64 for allowing connection to an external speaker for the above-described reasons.

A switch 74, having a number of positions, is disposed on the control box 58 for switching between groups of sounds, for example exemplary normal and abnormal sounds that may be those heard in an adult, neonate, or fetus. An RF (radio frequency) signal acquisition coil 76, such as is available from M.C. Davis Co. (Arizona City, Ariz.), is disposed in the interior of the bell 56 for transmitting and acquiring RF signals, as will be explained. The acquisition coil 76 is a copper coil and circuitry having an associated wire 76*a*, which is attached to the electronic control box 58. A polymeric disc 78 is disposed between the acquisition coil 76 and the bell 56 to decrease noise from the bell.

In other embodiments, the sounds are recreated by speakers (not shown) disposed within the manikin such that the sounds are audible without the use of a real or virtual stethoscope. In yet other embodiments, the sounds are recreated by speakers (not shown) disposed within the manikin such that the sounds are audible with the use of a real stethoscope.

Referring to FIG. 3*b*, the sensor 30*j* is disposed beneath the skin 14*b* of the simulator 14 to avoid visual detection by the user. Likewise, it is advantageous that the sensor 30*j* have a minimal thickness to prevent intentional or accidental detection, as some anatomical locations, for example, intercostal spaces, must be palpated in order to be located. In an alternative embodiment, the sensors 30*j* may be affixed to an overlay (not depicted) substantially similar to the skin 14*b*, thus allowing the overlay to be placed over other simulators and models of patients, thereby converting those devices to allow them to be used with the stethoscope 12*j*.

The sensor 30*j* comprises an RF ID tag 80, such as is available from Microchip Technology, Inc. (Chandler, Ariz.) (Part No. MCRF200-I/3C00A), which may be programmed using "Developer's Tools" also sold by Microchip Technology, Inc. to engender a unique signal that serves to identify the particular sensor 30*j*. A coil 82, such as is available from M. C. Davis Co. (Arizona City, Ariz.), is operably connected to the tag 80. The tag 80 and coil 82 are potted in RTV potting material 84, or silicon rubber, such as is available from M. C. Davis Co. (Arizona City, Ariz.), to prevent damage. Once potted, the tag 80 and coil 82 collectively form a COB module 86 which emits a signal comprising a unique train of frequencies when interrogated.

In operation, the COB module 86 may actively broadcast the frequencies, but preferably the COB module is passive, that is, only activated when interrogated by the acquisition coil 76 in the stethoscope bell 56. In this preferred embodiment, the acquisition coil 76 delivers a carrier signal, such as a 125 kHz excitation frequency, which is received by the COB module 86 when the bell 56 is brought within a predetermined proximity, or acquisition distance, of the COB module. The acquisition distance of the bell 56, and therefore the acquisition coil 76, to the COB module 86 is determined by the strength to noise (S/N) ratio of the carrier signal. Thus, adjustment of the S/N ratio of the carrier signal provides a means for controlling the precision with which the user must place the stethoscope bell 56 in relation to the anatomical location of the sensor 30*j*, and therefore the COB module 86. Precise placement of the bell 56 on the simulator 14 by the user is rewarded with feedback, in the form of an appropriate body sound. Normally, the S/N ratio is set to require that the bell 56 be brought within approximately one-half to two centimeters of the COB module 86 of the sensor 30*j*.

In response to receiving a sufficiently strong carrier signal, the COB module 86 emits a train of two identifying frequencies for use in a process conventionally known as frequency shift keying (FSK), although other keying methods could be used. The acquisition coil 76 in the stethoscope bell 56 receives the emitted frequencies and relays the signal to the acquisition circuit 68, which determines the identity of the sensor 30*j*. As the anatomical position of each sensor 30*j* is known to the programmer, a selection of appropriate body sounds associated with each sensor is provided, and accessible to the sound circuit 70. Thus, by identifying the sensor 30*j*, the acquisition circuit 68 directs the sound circuit 70 to play an appropriate body sound for the anatomical position of the COB module 86, which is heard by the user through the speaker 72 disposed in the earpiece 50*a*. It can be appreciated that to expose the user to a greater selection of sounds, more sensors 30*j* could be added to the simulator 14, or each sensor could correspond to more than one sound. As depicted, the switch 74 has five different positions, and includes means for switching the sound circuit 70 between five different groups of sounds. Thus, it is understood that the number of switch positions corresponds to the number of sounds that can be produced by a single sensor, i.e., with thirteen sensors and five switch positions, the user could listen to up to sixty-five location-appropriate sounds, including examples of normal and abnormal sounds.

It can be appreciated that the above-described acquisition coil and COB module may be adapted to be used with the respective leads, paddles, or probes ("connectors") of the ECG monitor 12*c*, the temporary external pacer 12*f*, the automatic external defibrillator (AED) 12*g*, the manual defibrillator 12*h*, the ultrasound wand 12*i*, and the fetal distress monitor 121. If desired, the connectors may be equipped with adhesive to temporarily hold them in place on the patient simulator. The interaction between the instruments' connectors and the sensors 30, as sensed by the CIM 16, confirms proper placement. The hidden location of the sensors 30 beneath the skin of the patient simulator further challenges a user's patient care skills, as well as more closely mimicking a real patient.

It is understood that the simulator 14 is designed to represent a patient and receive treatment, and as such the simulator 14 could take a variety of forms, including a fully articulating and adult-sized obstetrics simulator, a curled fetus, an articulating fetus, multiple fetuses, or a neonate, as well as a portion of simulated patient, for example, the torso and pelvic region.

Figure 4:
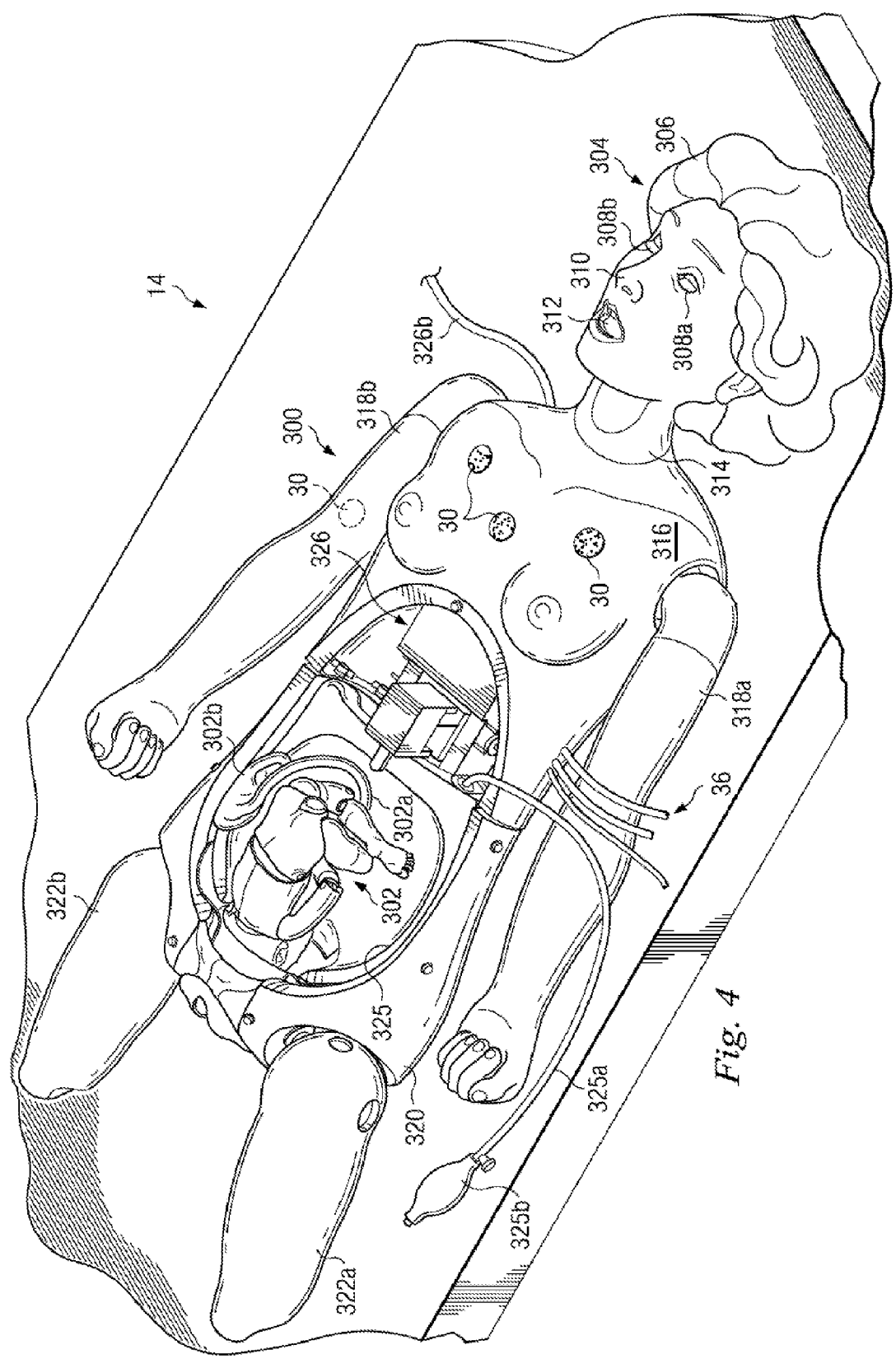
FIG. 4 is a perspective view of an illustrative embodiment of a patient simulator.
Figure 5A:
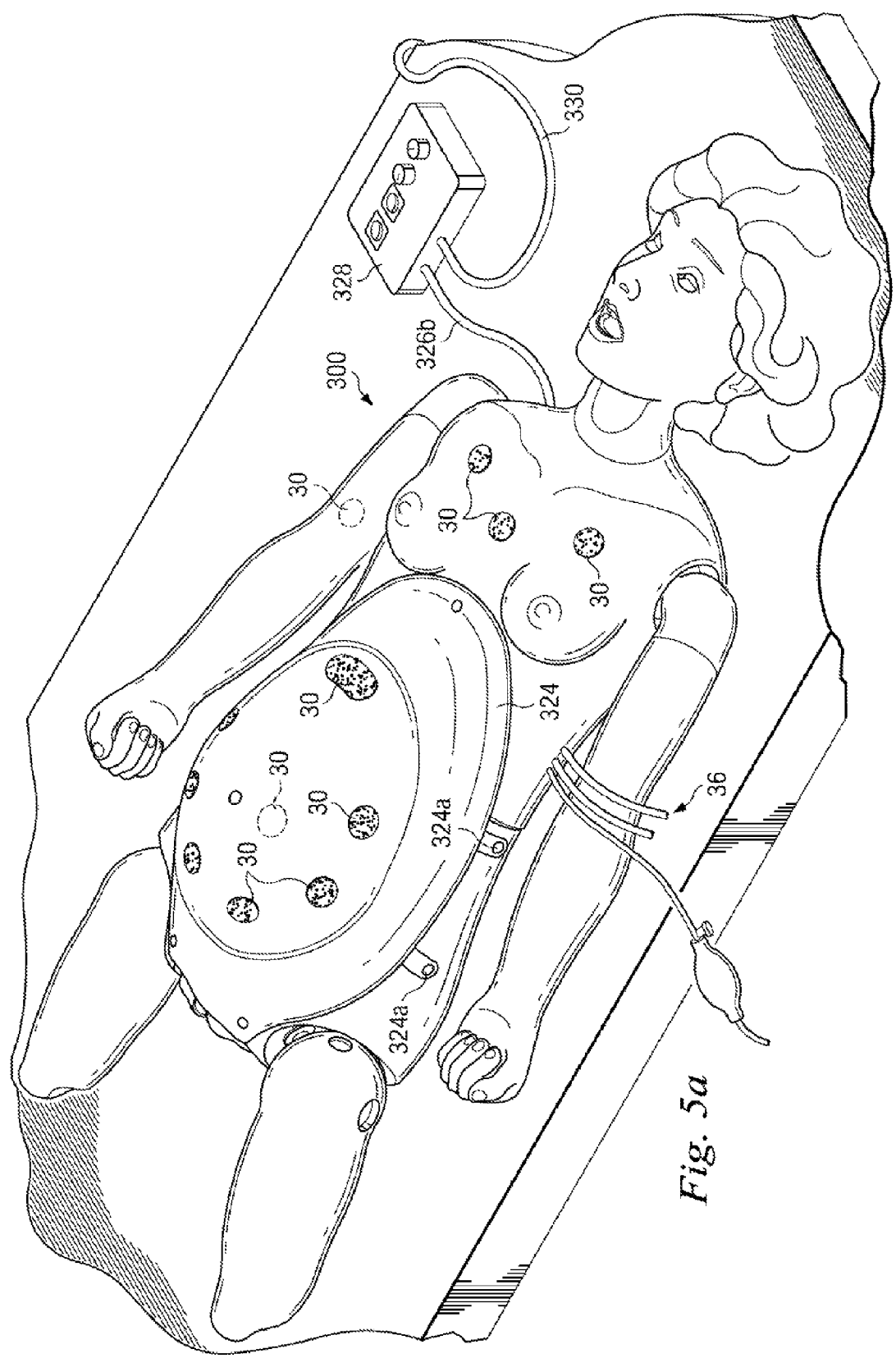
FIG. 5a is a perspective view of the patient simulator of FIG. 4 with an attached cover.

Referring to FIGS. 4 and 5*a*, in an illustrative embodiment, the simulator 14 comprises a child birthing maternal simulator 300 and a removable associated fetal simulator 302. The maternal simulator 300 has a head 304, with hair 306, eyes 308*a-b*, a nose 310, and a mouth 312. The head assembly contains a realistic airway (not depicted) capable of accepting conventional airway adjuncts. Sensors, generally denoted 30 (FIG. 1*a*), may be disposed on the skin of the maternal simulator (shown as stippled) and/or beneath the skin (shown in phantom). It is understood that in one embodiment of the maternal simulator (not depicted), no sensors are associated with the simulator. Lines 36 protrude from the torso 316 for providing electrical, pneumatic, or fluid connections, as well as for connecting the sensors 30 to the CIM 16, if necessary.

In other embodiments, the maternal simulator 300 is tetherless. That is, the maternal simulator is functional without wired or tubular connection to other devices outside of the simulator and, therefore, does not have lines 36, 325*a*, and 326*b* extending from the torso 316. Rather, the maternal simulator is self-contained. Thus, the maternal simulator 300 can include an internal power supply, such as a rechargeable power cell, and all pneumatic and fluid connections are made to the corresponding compressors or other devices within the maternal simulator 300. As the maternal simulator is self-contained, it is not only portable, but can be in use while being transported between different locations. Further, in such embodiments, the maternal simulator 300 may communicate with other devices, such as the CIM 16, through wireless communication. Thus, the entire simulator system 14 can be functional up to the limits of the wireless communication. Further, in some embodiments the maternal simulator 300 may connect to a computer or network system wireless, which then connects to the CIM 16 via a wired or wireless network, making the functional distance of the maternal simulator virtually limitless. Though only the maternal simulator has been described here as being self contained, the fetal and neonatal simulators described in more detail below are also tetherless in some embodiments. In some embodiments, the simulators are configured to be used both un-tethered and tethered. In some embodiments, the simulators are fully-functional when used un-tethered (i.e., the simulator has the same functionality tethered and un-tethered.)

A pair of arms 318*a-b* are connected to the torso 316. At least one arm contains an IV receptacle (not depicted) capable of accepting medications, and sensors 30*a* may be placed within the receptacle to ascertain whether an IV has been started. Similarly, the arm may contain a sensor 30*d* for auscultation of Korotkoff sounds, as well as means for measurement of blood pressure. A pelvic region 320 of the torso 316 receives a pair of legs 322*a-b*.

Referring to FIG. 5*a*, a cover 324 may be attached to the torso 316 via a plurality of snaps 324*a*, although other reversible fastening means, such as hook and loop closures may be used. The cover 324 retains sensors 30, for cooperating with the ultrasound wand 12*i*, fetal distress monitor 121, and the stethoscope 12*j*, or alternatively at least one small speaker, to allow simulation of fetal heart sounds which may be detected by the stethoscope 12*j* or a conventional stethoscope, respectively. In one embodiment, the cover 324 surrounds an open cell foam (not depicted) connected to means for producing a vacuum. Activation of the vacuum shrinks the foam, making it feel harder, which simulates uterine contractions by the maternal simulator 300. Alternatively, the cover 324 may retain an air bladder and associated line (not depicted) for pressurizing the cover, thus making it feel harder. In yet other embodiments, the cover may contain a plurality of flexible tubes (not shown) extending across the torso. The air pressure in the tubes determines the hardness. The pressure is adjusted to change the hardness. It is understood that different levels of hardness may be produced to simulate different levels of contraction strength, for example, mild, moderate, and strong contractions. If connected to the CIM 16 and program 15a, the contractions could be spaced at regular intervals, and associated data for maternal intrauterine pressure may be displayed by the program, as will be discussed with FIG. 14.

Returning to FIG. 4, the fetal simulator 302, has an umbilical cord 302a and placenta 302b, and is depicted as resting upon a removable stage 325 disposed inside the maternal simulator. The removable stage 325 has a bladder (not shown), a line 325a, and a bulb 325b. When the bulb 325b is used to pump air into the bladder, the stage 325, and hence the fetal simulator 302, is raised relatively upwards. When covered with the cover 324 (FIG. 5a), raising of the stage 325 allows a user to palpate the fetal simulator 302 through the cover to assess position, as well as to perform Leopold maneuvers. In other embodiments, the bulb 325b is replaced by an alternative pump, such as an electrically powered, pneumatic pump. The electric pump may be controlled remotely through a computer system or other device.

A birthing device 326 is disposed inside the torso 316, as will be described. The cover 324 is designed to obscure the fetal simulator 302 of the simulator and the birthing device 326 from view, thus more accurately simulating the child birthing process, and challenging the user's diagnostic abilities. With the stage 325 removed, the birthing device 326 may be operated via a manual crank (not shown), or by a small motor 326a connected via a line 326b to controlling means for turning the motor on or off, as well as determining operational speed.

Figure 5B:
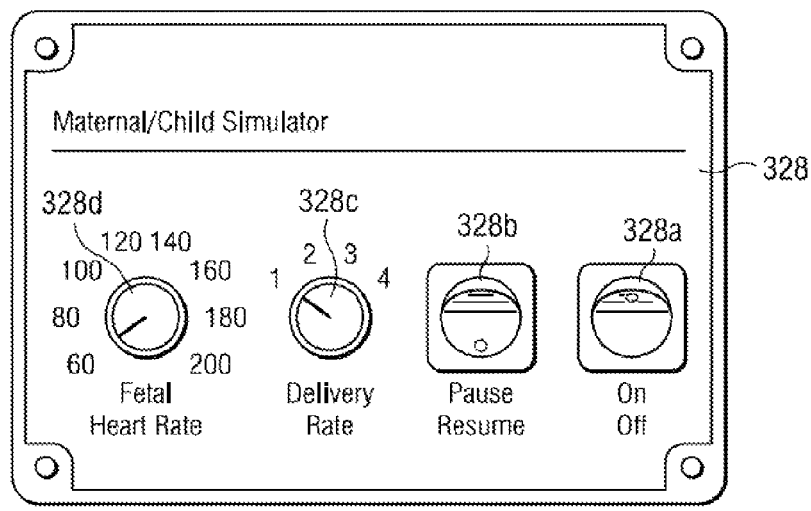
FIG. 5b is a top plan view of a control box.

In a first embodiment, software of the program 15a controls the birthing device 326, as will be discussed in conjunction with FIG. 14, below. In an alternative embodiment, the controlling means is a control box 328, and a line 330 which connects the control box 328 to the CIM 16. Referring to FIG. 5b, the control box 328 has controls 328a-d for respectively turning the simulator 14 on and off, pausing and resuming child birthing, determining the speed of the delivery rate, and setting the fetal heart rate.

Figure 6:
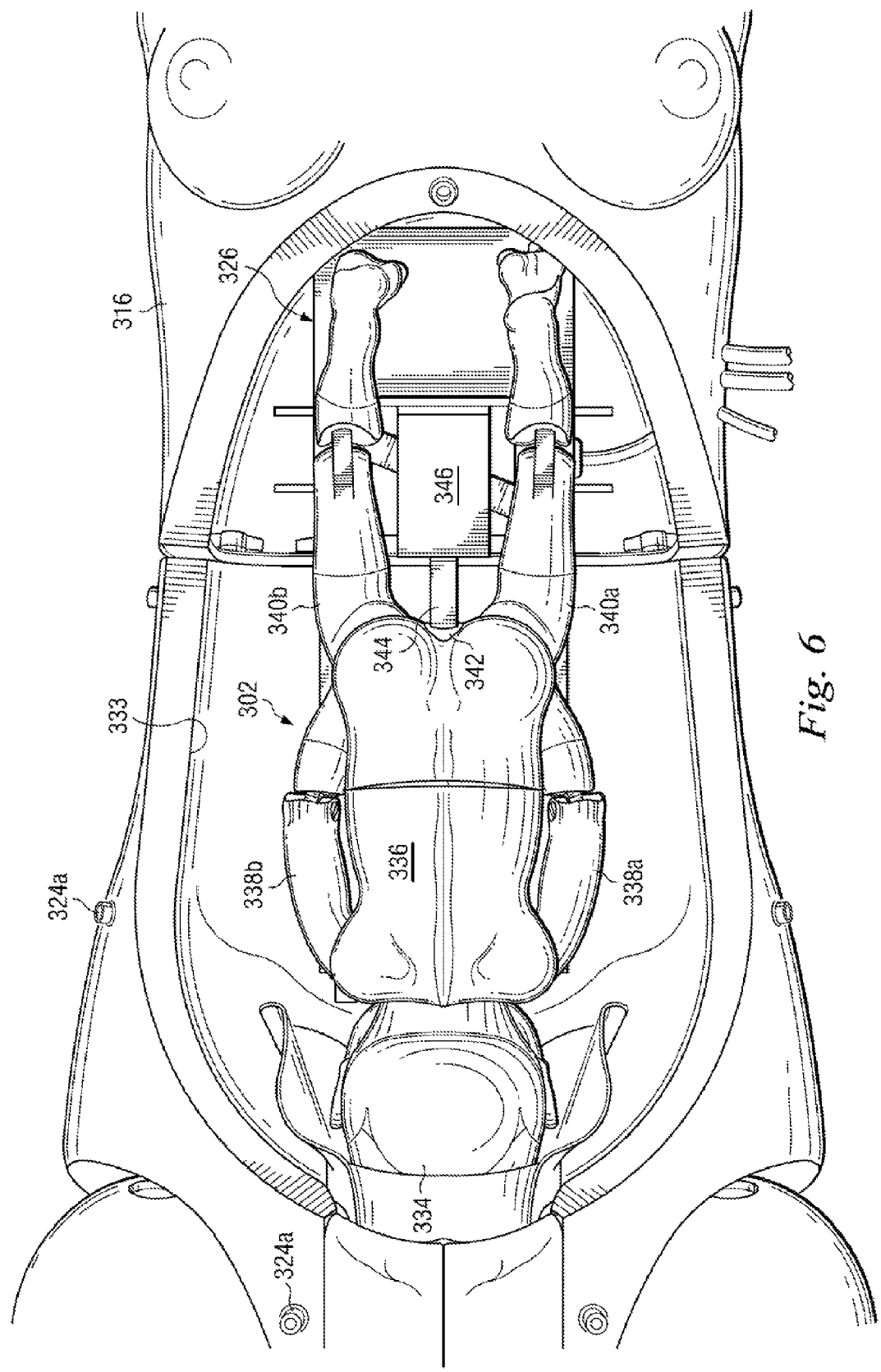
FIG. 6 is a perspective view of the torso of the patient simulator of FIG. 4.
Figure 7:
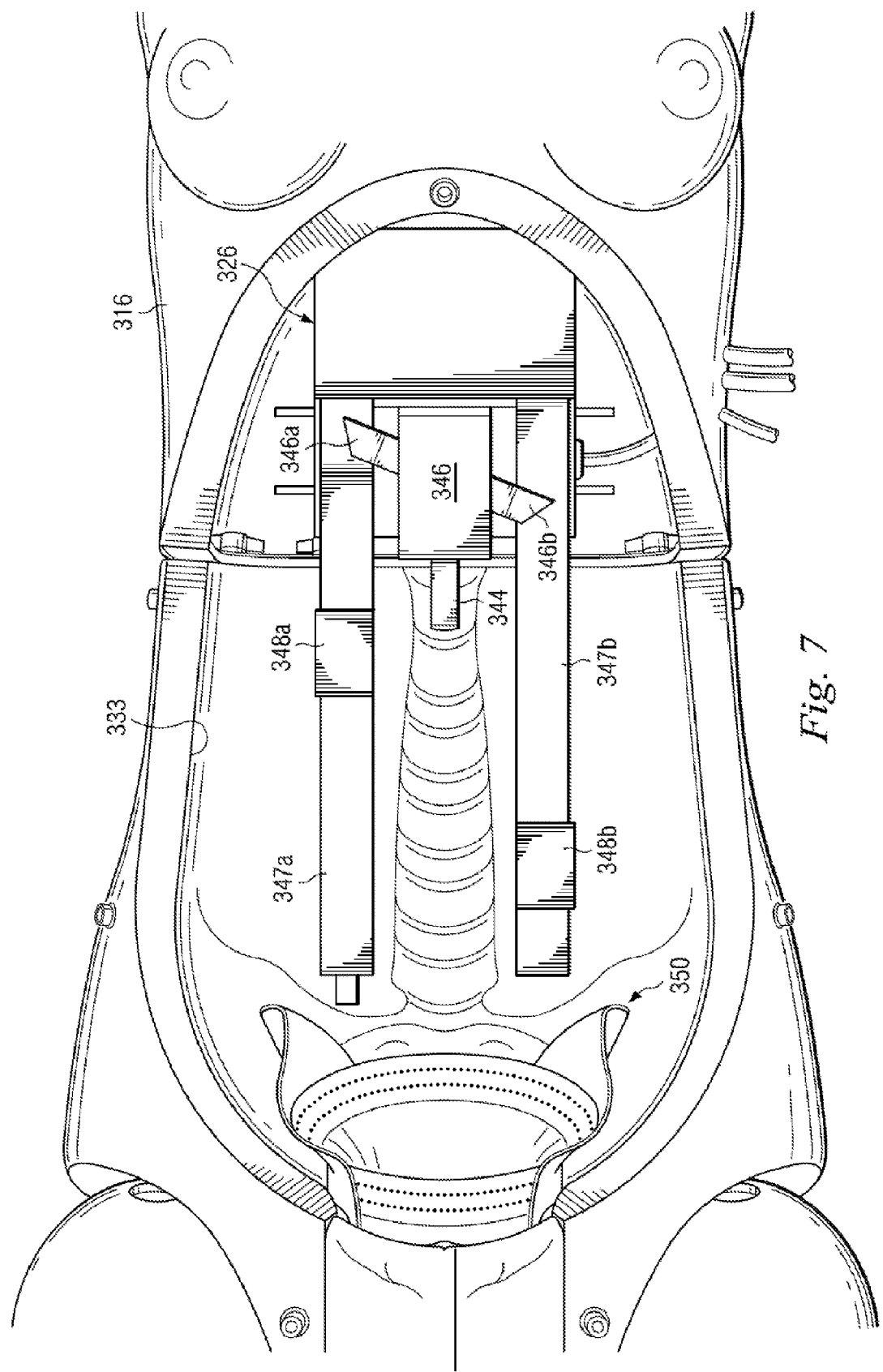
FIG. 7 is a perspective view of FIG. 6 with the fetal portion of the patient simulator removed.

Referring to FIGS. 6 and 7, the torso 316 of the maternal simulator 300 is shown with the cover 324 removed to expose the fetal simulator 302. The fetal simulator 302 is disposed in a cavity 333 of the maternal simulator 300, and has a head 334, an attached torso 336, with a pair of arms 338a-b and legs 340a-b attached to the torso. The head 334 is soft to allow for vacuum extraction, and has a mouth and nose which may be suctioned by the user.

In that regard, in some embodiments the fetal simulator 302 includes force sensors (not shown) positioned in the neck, shoulders, and hips to monitor the amount of force being applied on the fetal simulator during delivery. Pulling on the head 334 produces a signal from the neck sensor. The amount of force is relayed to the user and/or instructor by a user interface. The user interface can include a graphical display or audible signals. For example, the user interface may produce a bar graph indicating the amount of force being applied or the user interface may beep or otherwise sound an alarm when the force exceeds a predetermined threshold, prompting the user to reduce the force being applied or try a different delivery method. In one embodiment, the maximum force threshold is approximately 40 lbs. of force. In one embodiment, the preferred range of force is between approximately 17-20 lbs. of force. Shoulder dystocia is a potentially fatal situation wherein the shoulder of the fetus becomes lodged behind the maternal pubic bone. Too much force can lead to brachial plexis and even Erb's palsy in the fetus. To simulate this potential situation, shoulder sensors are included at the left and right shoulders of the fetal simulator 302 to monitor the force being applied at the shoulders. Finally, various situations, such as vaginal breeches, can cause the legs 340a-b to be grasped and removed from the vagina. The hip sensors serve to monitor the force being applied to the fetal simulator 302 in such situations. In some embodiments, the sensors 30 are in communication with an output device operable to provide output signal indicative of the measurement a particular sensor is adapted to monitor. The output device may output a electrical signal, wireless signal, or any other suitable output signal.

The umbilical cord and placenta 302a-b (FIG. 4) are removed to simplify the illustration, but it is understood that the placenta 302b (FIG. 4) could be disposed in any number of common orientations, such as normal fundal, low placement, or placenta previa, and attached to the cavity 333 with conventional removable fasteners. Likewise, the umbilical cord 302a (FIG. 4) could be presented to replicate various complications, and may house connecting lines to the fetal simulator 302 to allow an umbilical pulse to be felt by the user, or to convey electricity to the fetal simulator 302, if necessary.

A receiver 342 is disposed on the fetal simulator 302 to allow the birthing device 326 to retain the fetal simulator. Other receivers, similar to the receiver 342, are contemplated on different portions of the fetal simulator 302, such as to simulate a breech birth, and as the fetal simulator 302 articulates, a variety of breech deliveries, such as full, frank, and footling may be simulated.

The birthing device 326 has a projection 344 of a ram 346 which cooperates with the receiver 342 of the fetal simulator 302 to retain the fetal simulator. In some embodiments, the receiver 342 and projection 344 are adapted for selective engagement such that the fetal simulator 302 is selectively engaged with or released by the maternal simulator 300. In the depicted embodiment, the ram 346 is driven by a drive system, including a small electric motor, gears, electronic logic to permit resetting, means to determine the position of the ram, and a forward and reverse function. The ram 346 proceeds down a set of tracks 347a-b, thereby translating the fetal simulator 302 out of the maternal simulator 300.

The projection 344 of the ram 346 is rotatable, the birthing device 326 thereby producing both rotational and translational movement of fetal simulator 302, to simulate a realistic child birthing scenario, wherein the fetus makes a turn to bring it to a normal nose down position of crowning, and it makes another turn after crowning to allow its shoulders to better pass through the birth canal. In some embodiments, the receiver 342 is disposed in another portion of the fetal simulator, such as the head, neck, shoulders, arms, hips, and/or legs. Alternative embodiments of the receiver 342 and projection 344 are discussed in relation to FIGS. 24-27 below.

In one embodiment, levers 346a-b of the ram 346, being operably connected to the projection 344, engage cams 348a-b, respectively, to produce rotation. As the ram 346 proceeds down the tracks 347a-b, the levers 346a-b of the ram engage the fixed cams 348a-b in turn, causing the respective lever to move. Movement of the lever rotates the projection 344. Eventually, the respective lever is moved to a point where the lever clears the respective cam. It can be appreciated that the cams 348a-b may be located at places along the tracks 347a-b where rotation is desired, the tracks simulating the birth canal. Thus, internal rotation of the fetus is produced by the lever 346a engaging the cam 348a, and external rotation of the fetus is produced by the lever 346b engaging the cam 348b. As described below in relation to FIG. 28, in some embodiments the cams 348a-b are moveable between a position for causing rotation of the fetal simulator and a position that does not cause rotation of the fetal simulator. Further, in some embodiments the cams 348a-b include intermediate position(s) to provide some rotation to the fetal simulator. Alternatively, the program 15a allows for adjustment of the rotation of the projection 344 from zero to one hundred and eighty degrees, as will be discussed with reference to FIG. 14, below. In either embodiment, the fetus 302 passes through a distensible cervix 350, as will be described.

Figure 9:
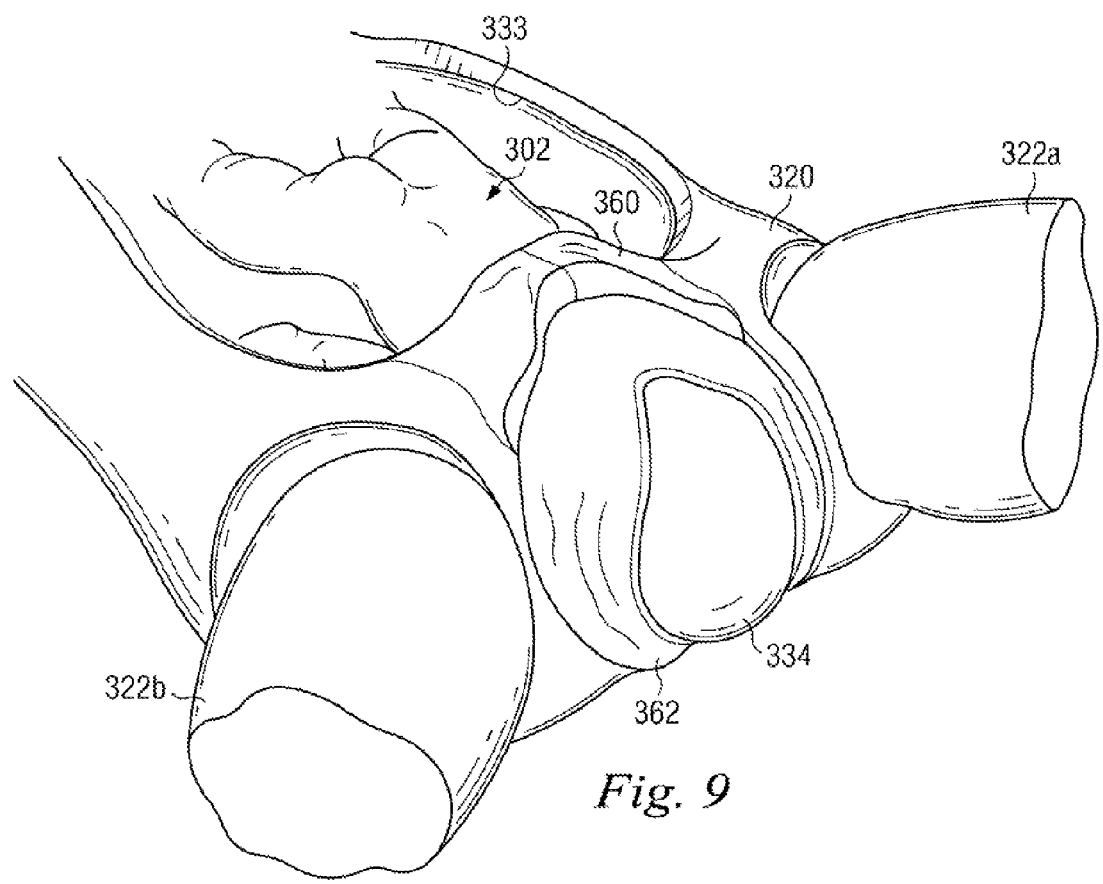
FIG. 9 is a perspective view of the exterior of the patient simulator.
Figure 8:
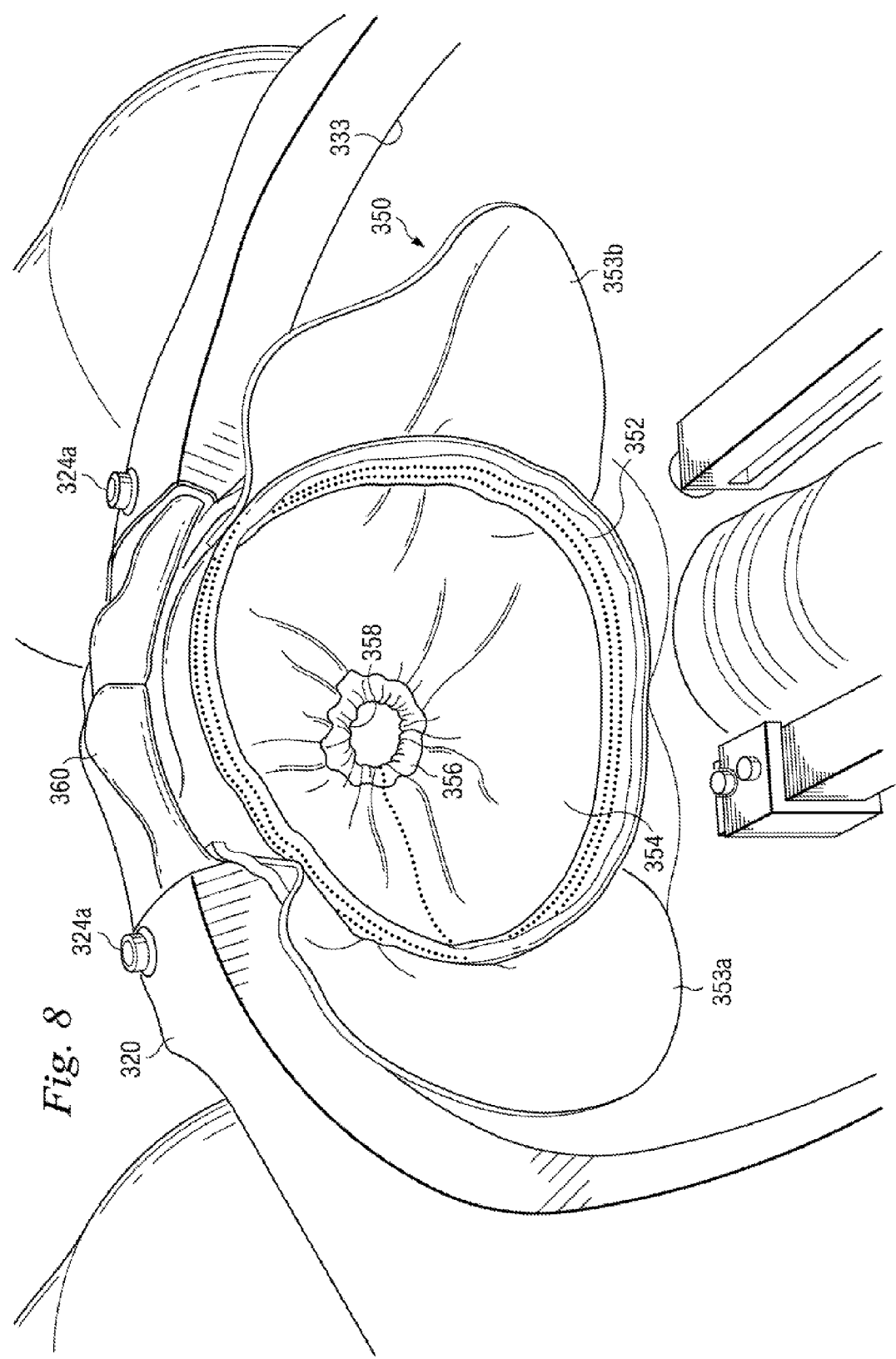
FIG. 8 is a perspective view of a distensible cervix of the patient simulator.

Referring now to FIGS. 8 and 9, the distensible cervix 350 comprises a ring 352 having attached flaps 353a-b for maintaining the cervix's position in the cavity 333. As such, the flaps 353a-b may have attached snaps, hook and loop closures, or other reversible fastening means. A wall 354 is connected to the ring 352, and is preferably of an elastic material, such as Lycra[7], or thermoplastic elastomer. A gathering 356 of the wall material defines a port 358. The gathering 356 may have an associated elastomeric element disposed interiorly to enhance the elasticity of the port 358. Alternatively, the wall 354 itself may provide sufficient elasticity.

The port 358 expands from about two to ten centimeters in diameter as the fetal simulator 302 is pushed through the port, and because of the shape of the fetal simulator's head 334, and the elasticity of the wall 354, dilation is automatically simulated coincident to fetal descent. The user may then practice measuring cervical dilation and plot labor progress as a Partograph. The elasticity of the wall 354 may be adjusted, for example by using thicker or thinner wall material, to produce a cervix having faster or slower dilation than normal, respectively. The cervix 350 is disposed concentric to the pelvic area 320, which has a pubic bone 360, as well as several cover snaps 324a.

The fetal simulator 302 moves through the cervix 350 and out of the cavity 333 past vulva 362. The vulva 362 are made of a flexible material so that the user may manipulate the vulva, or perform an episotomy to birth the head 334. It is understood that the vulva 362 may comprise a portion of an insert (not depicted) including features such as a urinary tract and rectum, which could be replaceable with other genital inserts for displaying various patient conditions. After delivery, the user may practice postpartum exercises, such as massaging a uterus insert (not depicted) back to a desirable size, removing retained placenta parts (not depicted), or repairing the cervix 350 or vulva 362.

In one embodiment, the torso 316 contains a simulated heart, lungs, and ribs. The heart (not depicted) beats by the action of a pulsatile flow which is controlled by the program 15a in response to the condition of the patient and upon therapeutic interventions. Palpable pulses may be found at carotid, brachial, radial, femoral, and pedis dorsis locations. Specific pulse locations become non-palpable as the systolic pressure falls, and the absence or presence of a pulse will depend upon the simulated blood pressure. Heart sounds are heard at appropriate locations through the use of the stethoscope 12j. The heart beat is synchronized with the Virtual EKGs, which are determined by the program 15a. Application of the stethoscope 12j to a point below the BP cuff 30d (FIG. 2) will cause the appropriate Korotkoff sounds to be heard.

The maternal simulator 300 displays a combination of ventilation means, and lung and airway sounds are heard at appropriate locations using the stethoscope 12j. The simulator 300 breathes spontaneously in a manner that would achieve targeted arterial blood gases for a given situation, including response to interventions such as ventilation and administration of drugs, and demonstrates the amount of chest rise relating to the tidal volume and physiologic states. Normal gas exchange lung dynamics are virtual and are controlled by the program 15a, which may also determine tidal volumes (TV), functional residual capacity (FRC), and expired carbon dioxide ($CO_2$). Airway resistance, lung and chest wall compliance are also controlled by the program 15a.

The heart and lungs are connected to pressure transducers confirming airway ventilation and cardiac compression. For example, an air line may be mounted in tracheal wall or lungs of the simulator 300 and connected to a sensor circuit connected to the CIM 16 so that when cardiopulmonary resuscitation (CPR) ventilation is performed on the simulator, the CIM 16 monitors the timing and magnitude of the pressure and volume of the ventilation procedure, via the air line and the sensor. Similarly, a compression bladder may be embedded within the heart or chest cavity of the simulator 300 for sensing and confirming proper timing and magnitude of a CPR chest compression procedure, when connected by an air line to a compression sensor circuit attached to the CIM 16. It can be appreciated that compression and ventilation data is acquired from pressure waves sensed by the CIM 16 through the lines 36. The blood pressure, heart rate, and oxygen saturation is virtually measured by the BP cuff 30d (FIG. 2) and the Pulse Ox cuff 30e (FIG. 2), although the data displayed is generated by the program 15a.

Figure 10:
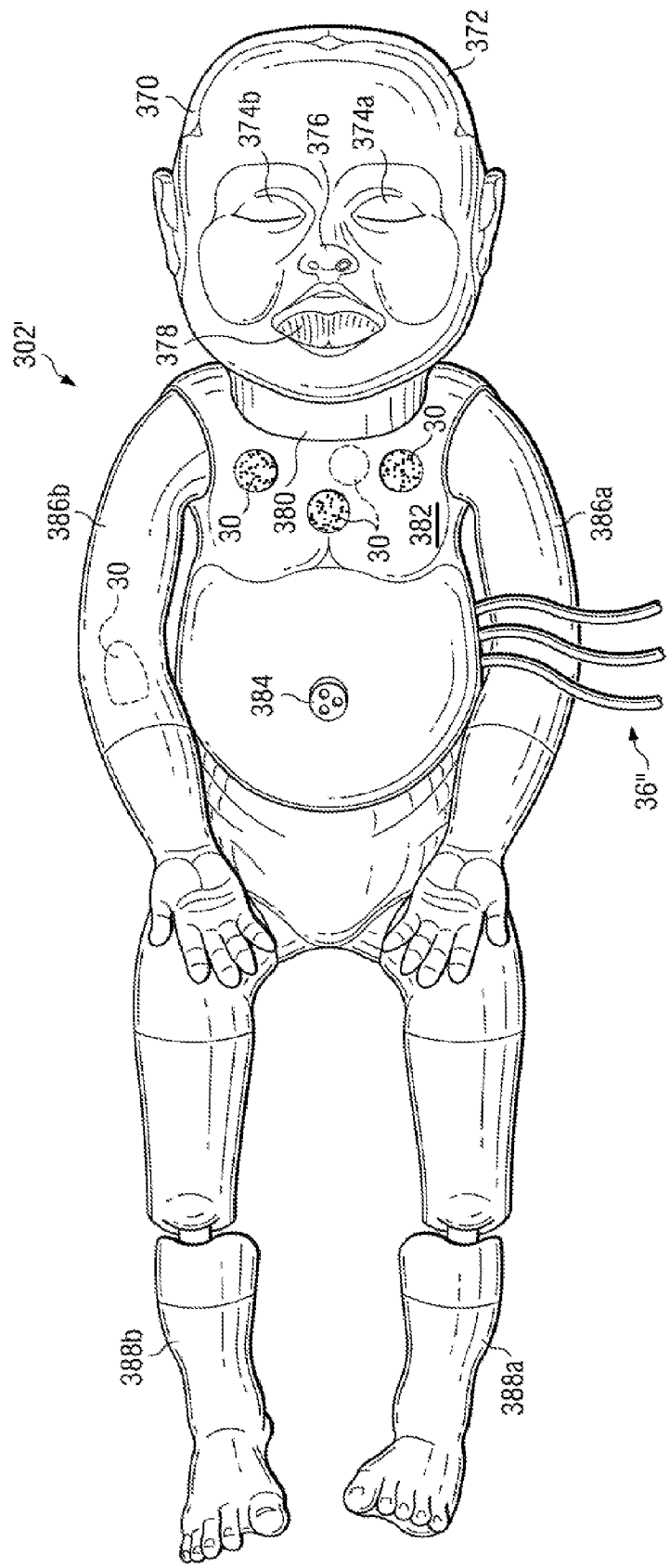
FIG. 10 is a perspective view of a neonatal embodiment of a patient simulator.

Referring to FIG. 10, a neonate simulator 302' may be used to replace the fetal simulator 302 (FIG. 8) to allow practice of neonatal resuscitation according to the program 15a. In other embodiments, the fetal simulator 302 is itself used in postbirth simulations. In that regard, the fetal simulator 302 can have all of the functionalities and features of the neonate simulator 302' as described herein. The neonate 302' has a head 370, with hair 372, eyes 374a-b, a nose 376, and a mouth 378. The head assembly contains a realistic airway (not depicted) capable of accepting conventional airway adjuncts and a sensor for determining whether an airway adjunct has been placed, or whether a fluid has passed. The head 370 is connected via a neck 380 to a torso 382.

Sensors, generally denoted 30 (FIG. 1a), may be disposed on the skin of the neonate simulator (shown as stippled) and/or beneath the skin (shown in phantom). Lines 36" protrude from the torso 382 for providing electrical, pneumatic, or fluid connection, as well as for connecting sensors (not depicted) to the CIM 16. The torso 382 has an umbilical site 384, which provides a site for catheterization, and a simulated heart, lungs, and ribs for performing CPR. The heart and lungs are connected to pressure transducers as described above for the maternal simulator 300 for confirming airway ventilation and cardiac compression. The neonate simulator 302' exhibits many of the same features as the maternal simulator 300 (FIG. 6), including heart rate, pulse, oxygenation, and a variety of body sounds which can be detected using the stethoscope 12j (FIG. 2) or a conventional stethoscope. A pair of arms 386a-b, and a pair of legs 388a-b, are also connected to the torso 3382.

In one embodiment, the hands and feet as well as the face and upper torso change color based upon proper oxygenation or an oxygen deficit. As oxygenation decreases, the extremities (peripheral cyanosis) change color first, followed by the face and upper torso (central cyanosis). Such change is reversible as oxygenation is improved.

In a preferred embodiment, coloration is achieved using blue thermochromatic dye (such as Reversatherm Blue Type F, available from Keystone, Chicago, Ill.), approximately 3 grams dissolved in 10 grams of clear vinyl paint thinner, and dispersed into 300 grams of clear vinyl paint. The mixture is applied to the hands, feet, chest, and face. At room temperature, the neonate is blue. Resistance heaters (such as available from Minco Products, Minneapolis, Minn.) are connected in parallel, and placed under the skin to provide 5-15 watts/in$^2$, or heat energy sufficient to raise the surface temperature of the skin to about 115°, causing the bluish color to disappear. Power for the heater is supplied through the CIM 16. The peripheral and central heaters may be separately controlled to allow peripheral cyanosis without central cyanosis. Heat sinks may also be disposed with the heaters to allow faster cooling, and hence, faster changes in coloration.

In one embodiment, the thermochromatic system is logically linked to the program 15a, for example, an instructor defines the condition of the neonate. Afterwards, coloration is responsive to CPR quality being performed by a user, either improving, worsening, or remaining the same. The program 15a also provides for an override if coloration changes are not desired. Coloration may alternatively be simulated by having applied a conventional photochrome to the simulator, such that upon exposure to an associated adjustable UV light, the simulator appears to turn blue. As another alternative, the coloration may be simulated by using colored lights. For example, in one aspect blue LEDs can be used.

As mentioned above with respect to the maternal simulator, in some embodiments the neonatal simulator does not include lines 36". Rather the neonatal simulator is tetherless such that is has self-contained functionality without the need for wired, tubed, or other physical connection to external devices.

Figure 11:
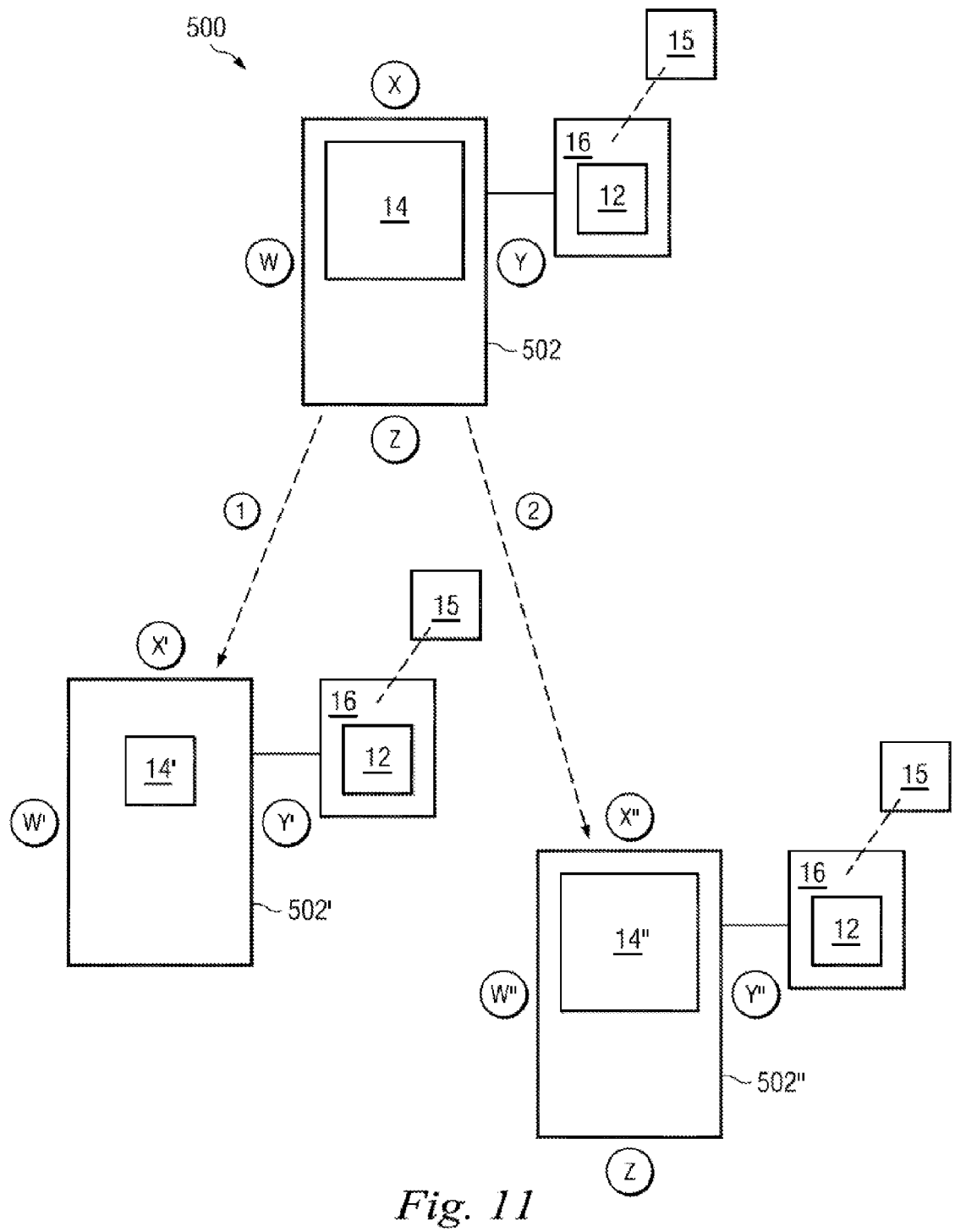
FIG. 11 is a schematic view of an illustrative use of the present system.

Referring now to FIG. 11, a child birthing system 500 illustrates the use of the foregoing embodiments. The simulator 14, for example, the maternal simulator 300 and fetus 302 are placed on a table 502. Students, W, X, Y, and Z, take places around the table, for example, W controls medication, Y controls virtual instruments 12, X controls anesthesia, and Z controls obstetrics. The child birthing device 326, as discussed above, may be driven via a manual crank or by a small motor 326a connected to either a control box 328, or the program 15a of the computer 15 may optionally (shown in phantom) control the birthing device 326. Whichever controlling means are used, the distensible cervix accurately reflects progress of the fetal simulator down the birth canal. Eventually, as described above, the fetal simulator is birthed.

Once the fetal simulator is birthed, a team W', X', and Y' (which are understood to be the same students W, X, and Y, or others depending on class size) moves along path 1 to practice neonatal care on a table 502'. At least one team, denoted by the absence of Z, must remain behind with the maternal simulator for monitoring and potential stabilization. The fetal simulator is switched with a neonatal simulator 14', for example, neonatal simulator 302' (FIG. 10). If connected to the computer, the program 15a may be used to simulate the need for neonatal resuscitation, and CPR and other emergency care protocols may be performed. The program 15a monitors the care received by the simulator via the CIM 16 and virtual instruments 12, and compares the care to accepted standards.

Meanwhile, the program 15a of the computer 15 may be used to simulate the need for maternal resuscitation. If so, a team moves along path 2 to practice maternal care on a table 502". Students, W", X", Y", and Z can work on the maternal simulator 14", for example maternal simulator 300 with the fetal simulator removed. CPR and other emergency care may be given, and the program 15a monitors the care received by the simulator via the CIM 16 and virtual instruments 12.

Figure 12:
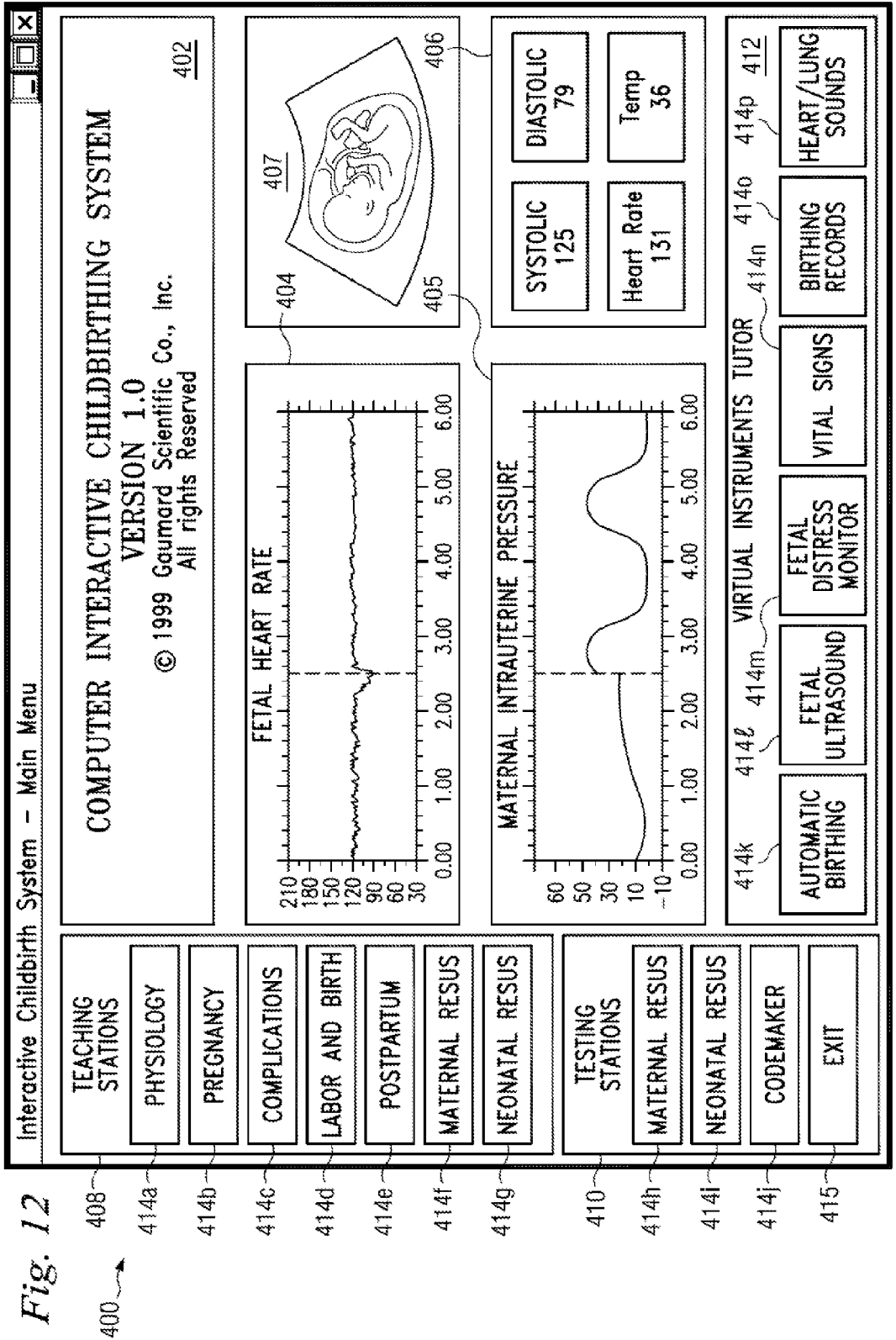

Referring now to FIG. 12, an introductory screen display 400 of the program 15a is presented on the computer 15 for teaching patient care protocols to a user. The display 400 includes several decorative features: a title box 402, a fetal heart rate box 404, a maternal intrauterine pressure box 405, a vital signs box 406, and an ultrasound video box 407. The display 400 also contains a teaching box 408, a testing box 410, and a virtual instruments box 412. As will be described, in some modules, the program 15a compares information pertaining to the user's activity with predetermined standards.

The screen 400 also displays a group of selectable patient care modules 414a-p provided by the program 15a, which furnish information on medical topics and associated concepts. Each module has a single topic, and represents an interactive patient care training session for the user. The modules 414a-g are disposed in the teaching box 408, and give an overview of relevant physiology, pregnancy, complications, labor and birth, postpartum, and maternal and neonatal resuscitation protocols. The modules 414h-j are disposed in the testing box 410, and give an opportunity to test a user in maternal and neonatal resuscitation protocols, as well as instructor defined protocols (Codemaker). An exit button 415 for exiting the program 15a is also disposed in the testing box 410. The modules 414k-p are disposed in the virtual instruments tutor box 412, and give a user a tutorial on use of the system, including automatic birthing, fetal ultrasound, fetal distress monitor, vital signs, Partographs, and heart and lung sounds.

Figure 13:
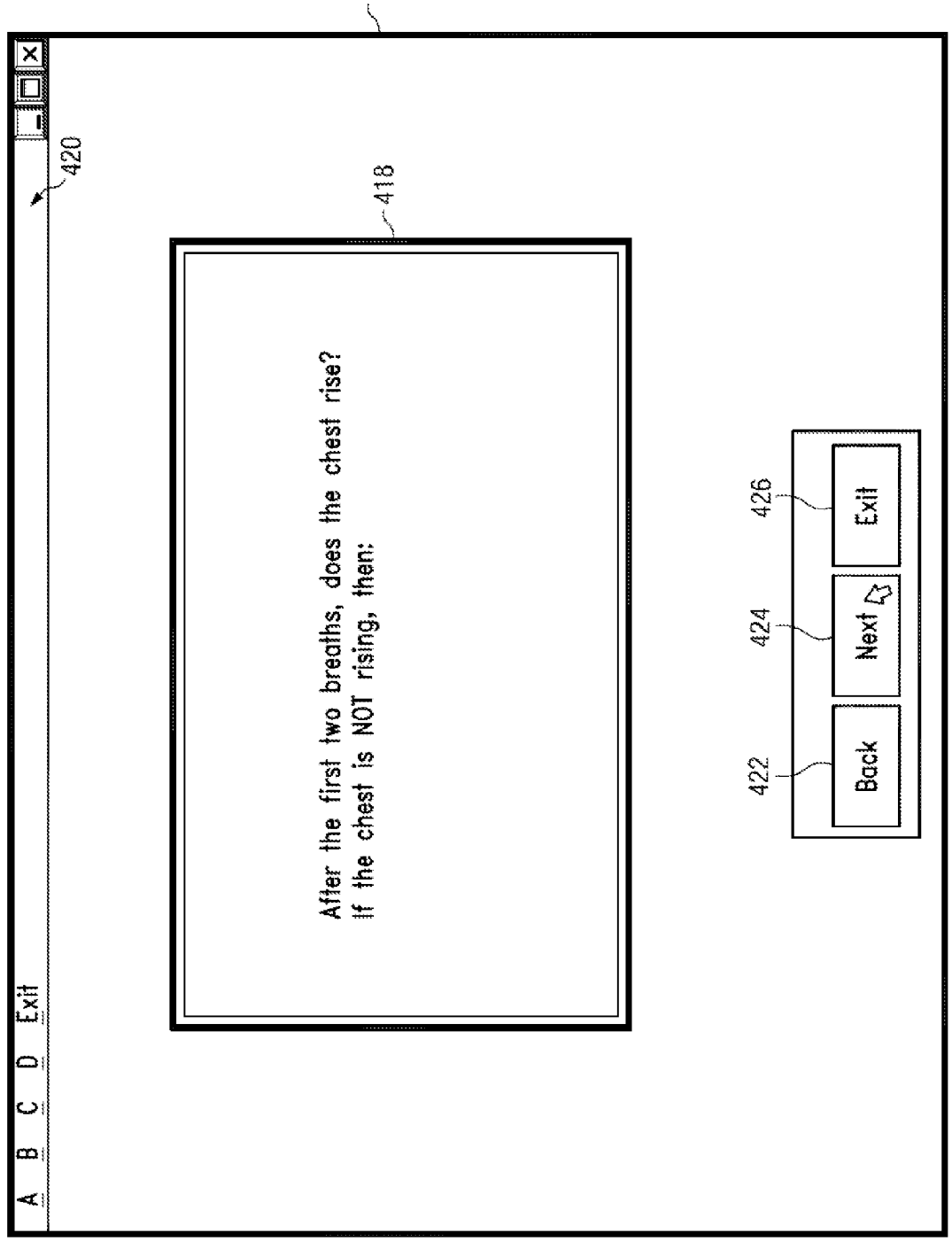

Referring to FIG. 13, if one of the modules (FIG. 12) is selected by the user, such as by voice recognition or selection with a mouse of the computer 15, the program 15a displays a display screen 416. The display screen 416 contains an information box 418, which contains topical information. The display screen 416 also has a menu bar 420 containing information items (illustrated as A-D for convenience) listing information categories specific to the topic of the selected module. It is understood that an item may be selected from the screen 416 via the menu bar 420, and that each module 414a-p has its own display screen with its own menu of specific informational items A-D, which may be expanded to include a large number of items, or condensed for example, by placing selectable sub-items under an item.

Selection of an item from a menu, other than an exit item, causes text and/or illustrations topical to the selected menu item to be displayed in the information box 418. In practice, the program may generate a new display screen (not depicted). As such, it is understood that the information screen 416 is used as an example of any number of screens, and furthermore, such screens can be displayed in sequential order, or a series, for each item. A series of screens, such as screen 416, comprises a tutorial regarding patient treatment protocols for the selected menu item. Thus, the user can review information from a library of topics by selecting the appropriate module, and item, and then navigating through a series. Navigation in a series of screens is attained by the user's selection between three boxes: 422, 424, and 426, respectively "Back", "Next", and "Exit", with corresponding function among the screens, such as proceeding backwards or forwards in the series. If no "Back" or "Next" function is possible, as respectively would be the case of the first and last screen of a series, the boxes 422 or 424 may be unselectable.

For example, modules 414*f* and 414*g*, each engender a series to teach a user about maternal and neonatal resuscitation, respectively. The user may also practice CPR on the simulator 14 (FIG. 1*a*), such as the maternal simulator 300, or the neonatal simulator 302', above, and the program 15*a* senses the user's compression and ventilation, via the CIM 16 (FIG. 1*a*) and sensors 30 (FIG. 1*a*). The heart and lungs of the simulator 14 are connected to pressure transducers confirming airway ventilation and cardiac compression; for example, an air line may be mounted in tracheal wall of the simulator 14 and connected to a sensor 30 connected to the CIM 16, so that when CPR ventilation is performed on the simulator, the CIM 16 monitors the timing and magnitude of the pressure and volume of the ventilation activity, via the air line and the sensor. Similarly, a compression bladder may be embedded within the chest cavity of the simulator 14 for sensing and confirming proper timing and magnitude of a CPR chest compression procedure, when connected by an air line to a compression sensor 30 attached to the CIM 16. The program 15*a* compares the information pertaining to the user's activity with predetermined standards, and thus provides an interactive training session.

The predetermined standards are selectable, and reflect medical protocols used around the world, including BLS and ACLS guidelines set forth by the American Heart Association and others. At least seven major protocols for cardiopulmonary resuscitation (CPR) are stored and selectable by the user. Moreover, a user may update the protocols, or enter and store a "New Protocol" reflecting the local protocol regarding depth, duration, and frequency of cardiac compressions and airway ventilations. The program will use this series of acceptable limits to generate a new CPR waveform for testing CPR.

Referring back to FIG. 12, selection of a test module 414*h-j* from the test box 410 directs execution of the program 15*a* to provide a testing sequence to help test the user on patient care protocols, such as maternal and neonatal resuscitation, and other responses to emergency scenarios. The program 15*a* paces through the steps of a patient distress scenario, giving the user a predetermined time to respond or complete the task required, thus enabling the user to experience the pressure of a emergency situation. For example, the program 15*a* may test the user by presenting choices from which the user must select in order to treat the patient, wherein the user must complete the correct choice before the sequence proceeds to the next event. The program 15*a* enables the user to enable, disable, or check the virtual instruments 12 and sensors 30 for connection to supply input to the CIM 16.

If the virtual instruments 12 (FIG. 2) are enabled, the user may implement patient care activity on the simulator 14 using the virtual instruments 12, while having the results and quality of response being monitored by the program 15*a*. Alternatively, the user may use software-simulated instruments 12' (FIG. 1*b*) generated by the program 15*a*. The program 15*a* advances through the scenario until the patient recovers, and provides a running critique of the user's responses, with an explanation of each incorrect choice or action. Features of the test modules 414*h-j* include items that enable the user to specify that action sequences prescribed by the scenario comprise a predetermined number of compression/ventilation cycles on the simulator 14, or to allow the user to record the time and magnitude of the compression and ventilation activity performed on the simulator 14, or to select among a group of choices for hearing realistic sounds.

Testing may be defined by the program 15*a*, as above, or by the user. For example, selection of the Codemaker Test module 414*j* (FIG. 12) allows a first user, for example, an instructor, to create a scenario to test a second user, for example, a student. The first user may input preliminary data to define the patient simulator of the testing scenario by entering a set of preliminary patient parameters regarding information such as sex, weight, and age, as well as patient indications, vital signs and cardiac rhythms which will be realistically reflected in the vital signs monitor 406 (FIG. 12). An instructor defined testing system allows the instructor to test the student on local, national, or international patient care protocols. Many algorithms are selectable by opening files, including BLS, ACLS, Pediatric, and Obstetric (OB) emergencies. Other algorithms may be created and stored, and algorithms may be linked together as well. Benefits of this module include flexibility for instruction and the ability to detect mastery of the subject. An instructor-defined algorithm would presumably vary from well-known, structured algorithms, and thus avoid the problem of rote memorization of responses by the student.

Action may be taken in response to the conditions by the student, for example, the student may select among virtual instruments to use to render patient care activities. The student may then perform the patient care activities virtually, or using the tangible simulator.

Use of the modules 414*k-p* of the virtual instruments tutor box 52 provides information about instruments commonly used in child birthing scenarios. In some instances, opportunities to practice using some of the virtual instruments 12 in patient care protocols with the simulator 14 are provided.

Figure 14:
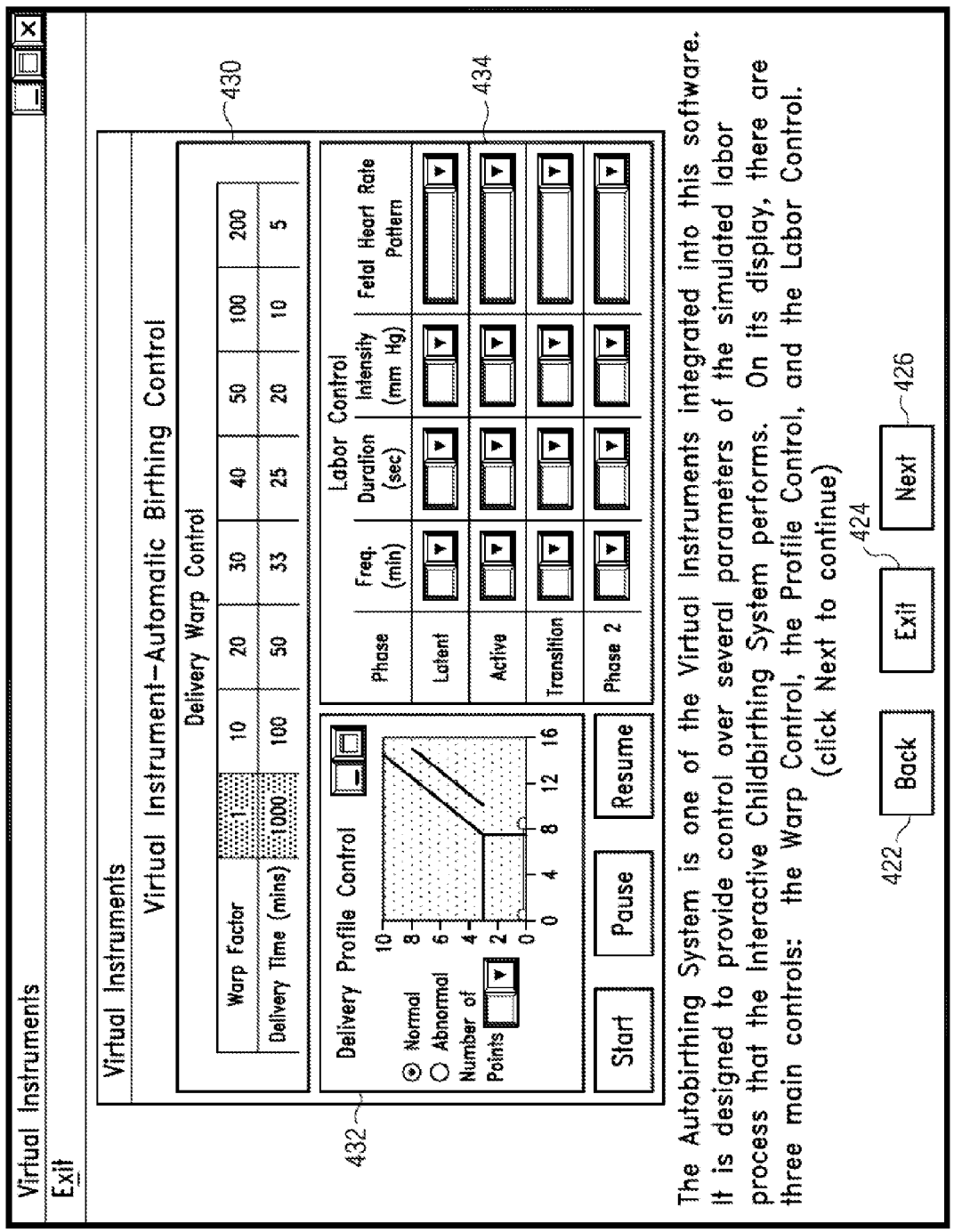
Figure 15:
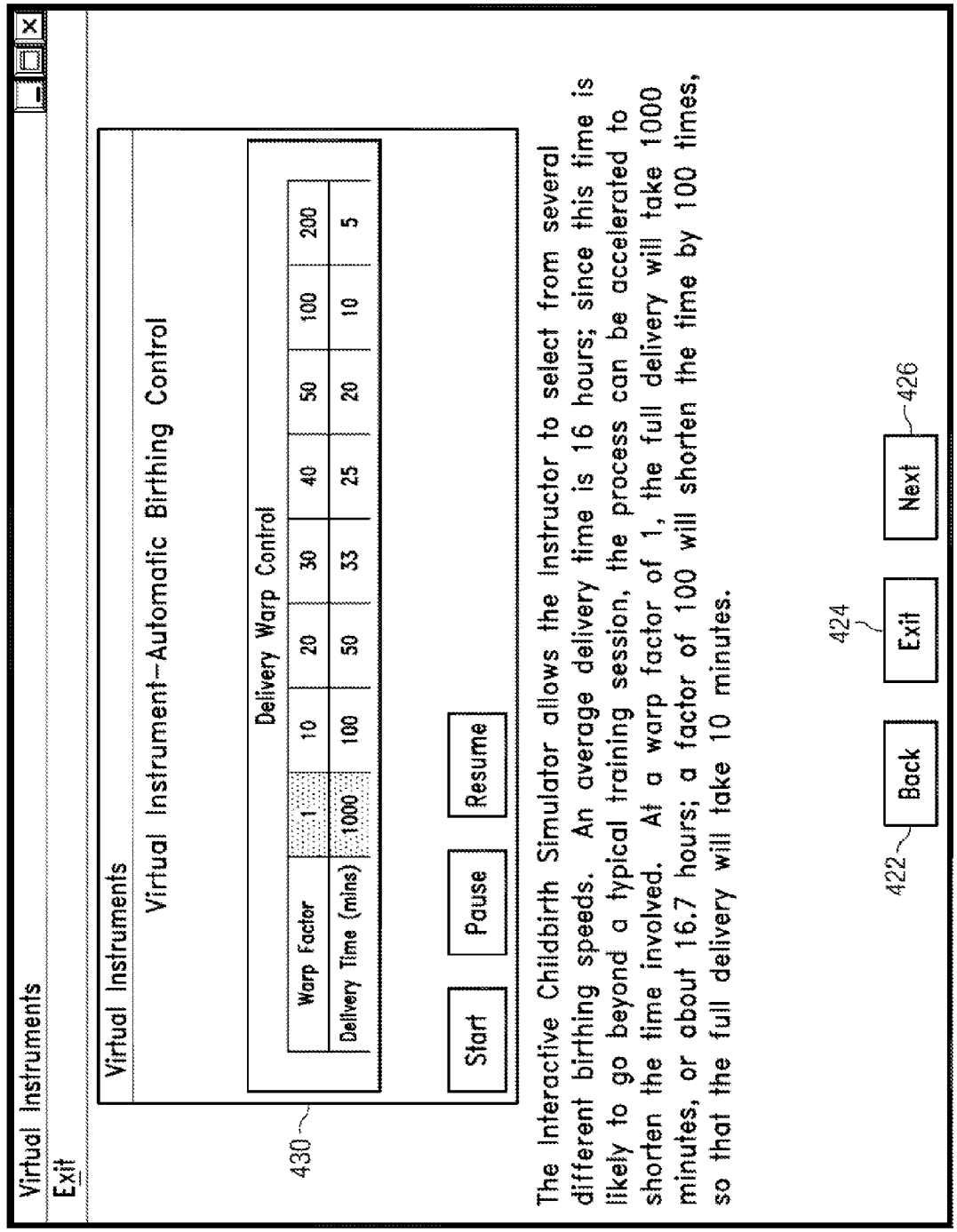

Turning now to FIGS. 14 and 15, the entire child birthing process may be automated via the program 15*a*, with the user merely defining initial conditions, such as delivery time 430, delivery profile 432, and contraction intensity 434. The warp feature allows a full delivery to be condensed from 16 hours to 5 minutes. Child birthing then consists of placing the fetal simulator 302 on the projection 344, and placing the cover 324 on the maternal simulator 300. The program 15*a* also offers a varying rate for progress of the ram 346, i.e., the first few centimeters may proceed much more slowly than the last few centimeters to better simulate child birth.

Figure 16:
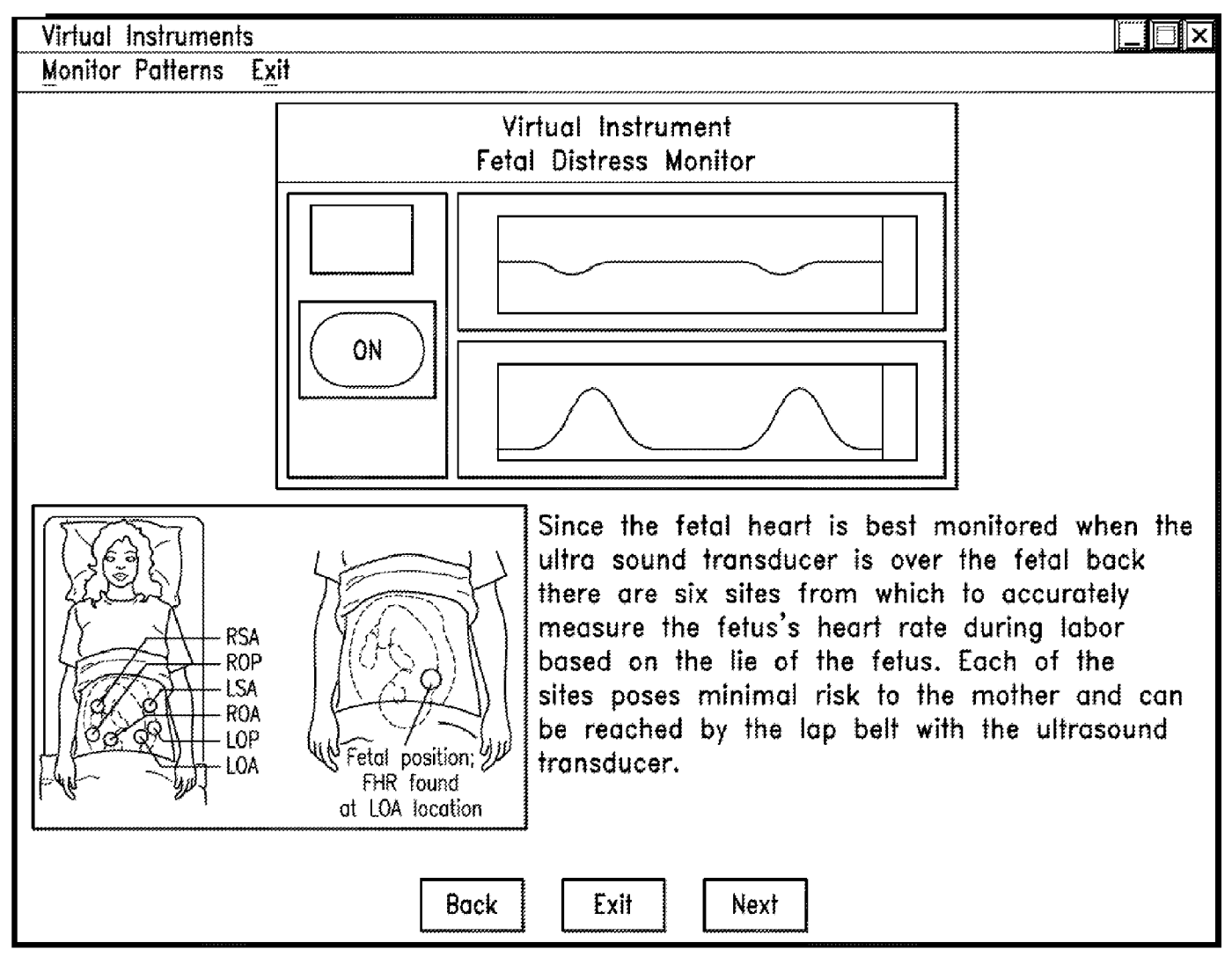

Referring to FIG. 16, if module 414*m* (FIG. 12) is selected, a series of screens are shown regarding the fetal distress monitor, with tutorial information. An exemplary fetal distress monitor box 436 is depicted, along with a selectable On button 436*a* for turning on the monitor. The fetal distress monitor 121 cooperates with the simulator 14, the fetal heart monitor is placed on the cover 324 of the maternal simulator 300 (FIG. 5*a*) and interacts with at least one sensor 30, while the contractions monitor interacts with another sensor 30 disposed on the cover.

Figure 17:
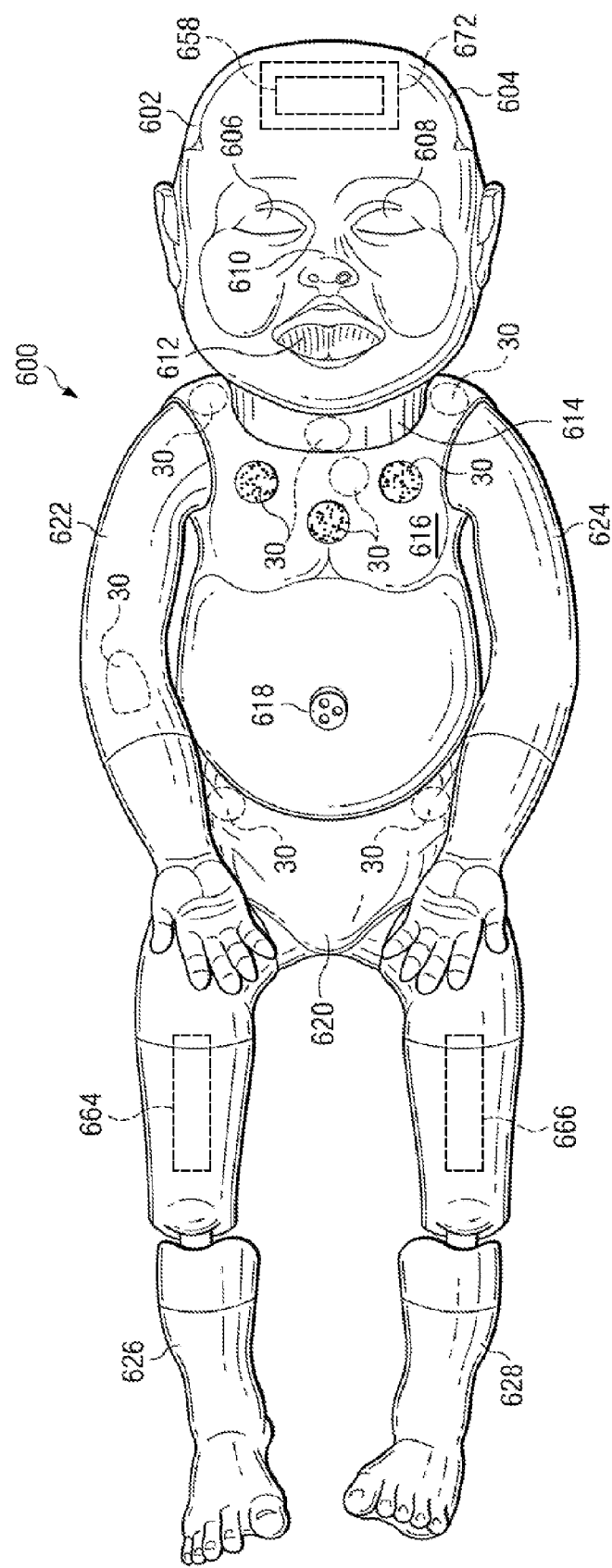
FIG. 17 is a perspective view of a neonatal embodiment of a patient simulator according to one embodiment of the present disclosure.

Referring to FIG. 17, a neonate simulator 600 may be used to replace the fetal simulator 302 to allow practice of neonatal resuscitation according to the program 15*a*. In one embodiment, the neonate simulator is substantially the size of an average sized neonate of 28 weeks gestational age. In another embodiment, the neonate simulator 600 is substantially the size of an average sized neonate of 40 weeks gestational age. The neonate simulator 600 exhibits many of the same features as the maternal simulator 300, including heart rate, pulse, oxygenation, and a variety of body sounds that can be detected using the virtual stethoscope 12*j* or a conventional stethoscope. Further, as described below the neonate simulator 600 is self-sufficient in that it does not require wired or tubed connection to any external devices for proper operation its numerous features, such as bulky external compressors and power supplies. The neonate simulator 600 is portable. In some embodiments the neonatal simulator is tetherless, such that it is functional without wired, tubed, or other physical connection to other external devices.

The neonate simulator 600 has a head 602, with hair 604, eyes 606 and 608, a nose 610, and a mouth 612. The head 602 is connected via a neck 614 to a torso 616. The torso 616 includes an umbilical site 618 that provides a site for catheterization. The torso 616 also includes an interchangeable genetalia site 620 that is adapted to receive both male and female genetalia pieces (not shown). Two arms 622 and 624 are connected to and extend from the upper portion of the torso 616. Two legs 626 and 628 are connected to and extend from the lower portion of the torso 616.

Sensors, generally denoted 30, may be disposed on the skin of the neonate simulator 600 (shown as stippled) and/or beneath the skin (shown in phantom) to provide various simulated features, as previously described. The torso 616 contains a simulated heart, lungs, and ribs for performing CPR. In one aspect, the heart and lungs are connected to pressure transducers as described above for the maternal simulator 300 for confirming airway ventilation and cardiac compression. The torso 616 also contains other components such as the power supply and wireless communication devices. In one embodiment, the power supply is a rechargeable pack of five lithium-ion cells. In one aspect, the power supply is positioned in the area normally reserved for the liver.

Figure 18:
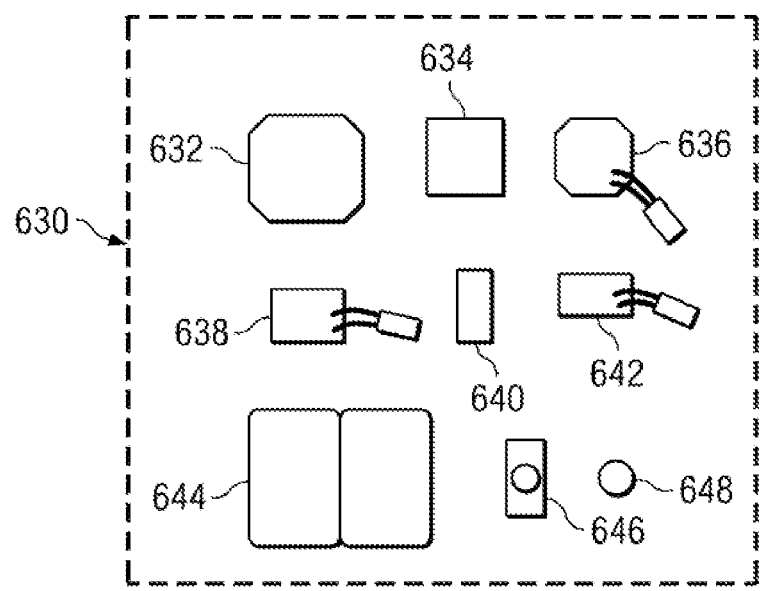
FIG. 18 is a perspective view of various modules for use with the neonatal simulator of FIG. 17.

To fit all of the functionality of the neonatal simulator 600 into a manikin the size of a neonate of 28 or 40 weeks gestational age, the numerous electronics must be appropriately sized and precisely positioned within the manikin where they are needed. In one embodiment, the electronic components of the neonate simulator 600 are grouped into smaller modules based on function, rather than placed on a general motherboard. For example, FIG. 18 illustrates one possible set of modules 630 for use in the neonate simulator 600. The set of modules 630 includes a master module 632 for interfacing the neonate 600 with the computer; a module 634 for generating the ECG signal; a module 636 for generating sounds such as heart, lungs, voice, and Korotkoff sounds; a module 638 for sensing pressure such as chest compression, airway ventilation, blood pressure, and compressor pressure; a module 640 for monitoring intubation; a module 642 for driving valves and LEDs; a module 644 for providing a connection such as a wireless interface and USB-RF interface; a module 646 for producing voice sounds; and a module 648 for producing sounds other than voice. One or more of these modules 632-648 can be combined to create any number of simulation features for the neonate simulator 600.

Figure 19:
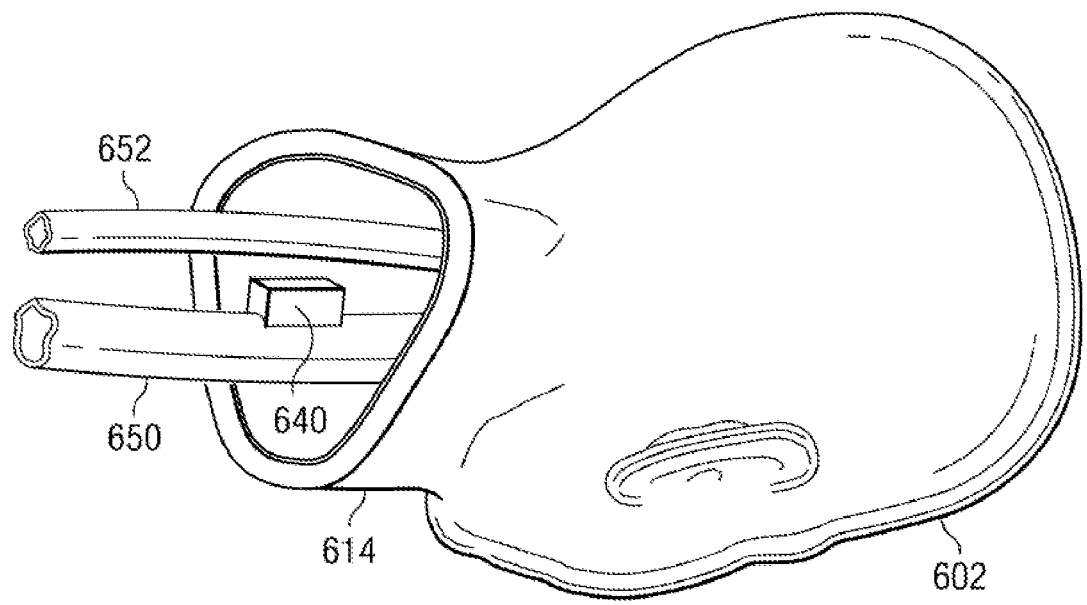
FIG. 19 is a perspective view of a cutaway portion of the neonatal simulator of FIG. 17.

Referring to FIG. 19, the neonate simulator 600 includes a realistic airway 650 accessible via the mouth 612 and nose 610. The airway 650 is capable of accepting conventional airway adjucts and a sensor, such as module 640, is positioned adjacent the airway for determining whether an airway adjunct has been placed, or whether a fluid has passed through the airway. In one embodiment, the module 640 is an optical sensor that monitors the position of an airway adjunct, such as an endotrachial tube, and determines the adjunct is positioned too high, too low, or just right. The neonate simulator 600 also includes a simulated esophagus 652 that extends into the torso 616 to a simulated stomach.

Figure 20:
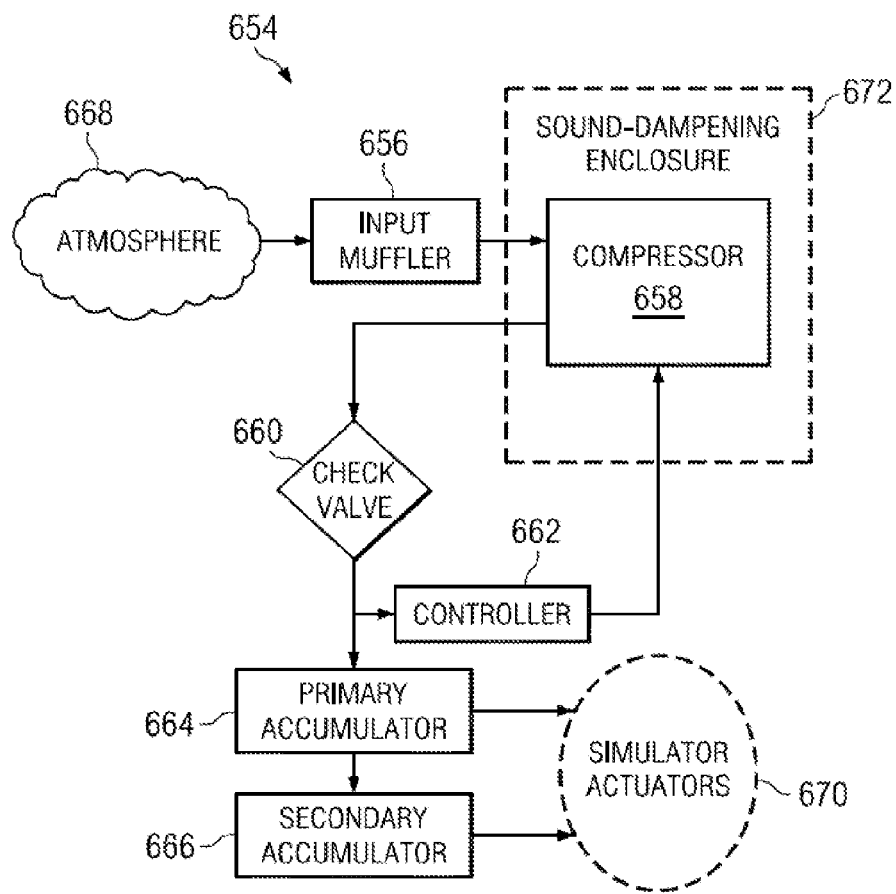
FIG. 20 is schematic view of an air supply system of the neonatal simulator of FIG. 17.

Referring to FIG. 20, the neonate simulator 600 also includes an air supply system 654 to simulate breathing, pulse, and associated physiological conditions of the neonate. The air supply system 654 includes a muffler 656, a compressor 658 (that may be a single diaphragm compressor such as model T2-03-E, available from T-Squared Pumps of New Jersey), a check valve 660 (appropriate valves may be obtained from Gulf Controls of Florida), a compressor controller 662, a primary accumulator 664, and a secondary accumulator 666. The compressor can alternatively be a rotary compressor or other suitable compressor.

In operation, the air supply system 654 provides pressured air to the neonate simulator 600 as follows. Air from the atmosphere 668 or a reservoir enters the compressor through the input muffler 656. The compressor controller 662 is utilized to maintain the pressure in the primary accumulator 664. A check valve 660 ensures air flow is in the proper direction. A pressure regulator (not shown) can be used to maintain a predefined pressure in the secondary accumulator. The primary and secondary accumulators are connected to actuators of the neonate simulator 600 for controlling supply of air. In one embodiment, the primary accumulator is connected to an actuator for controlling the supply of air to airway 650. In one embodiment, the secondary accumulator is connected to an actuator for controlling the supply of air to the lungs. The compressor controller 662 selectively provides power to the compressor 658 to maintain the desired pressure in the primary accumulator 664. In one embodiment, the approximate desired pressure of the primary accumulator is between 4.5-5.5 psi and the approximate desired pressure of the secondary accumulator is 1.5 psi. In some embodiments the air supply system 654 is further connected to the simulated circulatory system to provide simulated pulses or otherwise facilitate the simulated circulatory system.

The components of the air supply system 654 are positioned, insulated, and muffled to minimize the noise produced by the system. Since users will be utilizing stethoscopes to assess heart and breathing sounds of the neonate simulator 600, excessive noise from the air supply system 654 can interfere with and distract the user. To this end, portions of the air supply system 654 may be stored in the head 602 and extremities (arms 622, 624 and legs 626, 628) of the neonatal simulator 600.

For example, in one embodiment the compressor 658, the check valve 660, and the compressor controller 662 are positioned in the head 602 and the mufflers and accumulators are positioned in the legs 626, 628. The noise created by the components in the head is shielded by a sound dampening enclosure 672, illustrated schematically in FIG. 20. In one embodiment, the sound dampening enclosure 672 is a bilayer system having a first layer serving as an acoustic barrier and a second layer serving as a mass barrier. In one aspect, the acoustic barrier and the mass barrier are formed of noise abatement materials from EAR Specialty Composites. Further, the exhaust air created by the compressor 658 is ported down into legs 626, 628 of the simulator 600. Each leg 626, 628 includes a muffler system and an air reservoir. The muffler system dampens the "noisy" exhaust air to provide the air reservoir with a supply of "quiet" air for use by the neonate simulator 600 for the breathing and pulse simulations. In one aspect, the legs 626, 628 themselves serve as the air reservoirs and are sealed to prevent leakage.

Figure 21:
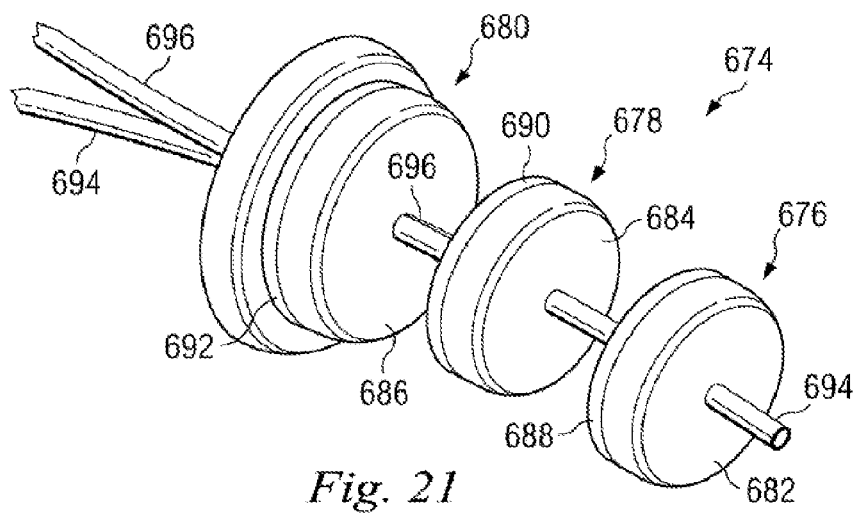
FIG. 21 is a perspective view of a cutaway portion of a muffler for use with the air supply system of FIG. 20.

FIG. 21 shows an exemplary embodiment of a muffler system 674. The muffler system 674 has three separate portions 676, 678, and 680 that dampen the sound from the noisy air. Each portion 676, 678, 680 has a first layer 682, 682, and 686, respectively, that serves as an acoustic barrier and a second layer 688, 690, and 692, respectively, that serves as a mass barrier. In one aspect, the acoustic barrier and the mass barrier are formed of the same noise abatement materials from EAR Specialty Composites as the sound dampening enclosure 672 described above. The noisy air is ported into the muffler system through a tube 694. The quiet or dampened air then exits the muffler through a tube 696. In one embodiment, the each leg 626, 628 is lined with noise abatement material in addition to the muffler system to further muffle and dampen any noise.

In one embodiment the hands and feet as well as the face and upper torso change color based upon proper oxygenation or an oxygen deficit. As oxygenation decreases, the extremities (peripheral cyanosis) change color first, followed by the face and upper torso (central cyanosis). Such change is reversible as oxygenation is improved. In one embodiment, the amount of time the neonate is without oxygen determines where the color and corresponding vital signs start, and the effort that is required to successfully bring the neonate back to healthy condition. In some embodiments, the simulator includes a mechanism for independently changing the color of the central portion and the peripheral portions. The mechanism, in some embodiments, utilizes blue LEDs or other lighting to simulate cyanosis.

In one embodiment, the thermochromatic system is logically linked to the program 15a, for example, an instructor defines the condition of the neonate. Afterwards, coloration is responsive to CPR quality being performed by a user, either improving, worsening, or remaining the same. For comparison, an adult can tolerate between 5-10 minutes without oxygen. A pregnant mother or the maternal simulator 300 uses oxygen more quickly than a normal adult and, therefore, is affected more quickly. A neonate, on the other hand, can tolerate on the order of 15 minutes without oxygen, with death in about 30 minutes. Thus, if the hypoxic event is 5-7 minutes the neonatal simulator 600 will "pink up" rather easily. If the hypoxic event is 12-15 minutes then recovery will be slower and requires more effort on the part of the user. Further, if the hypoxic event is more than 20 minutes, then it is very difficult even with the use of epinephrine for the user to get the neonatal simulator 600 to "pink up," and the neonatal simulator 600 can die or suffer some lifelong malady, such as cerebral palsy.

Figure 22:
FIG. 22 is a screen display view generated by a program according to one embodiment of the present disclosure.
Figure 23:
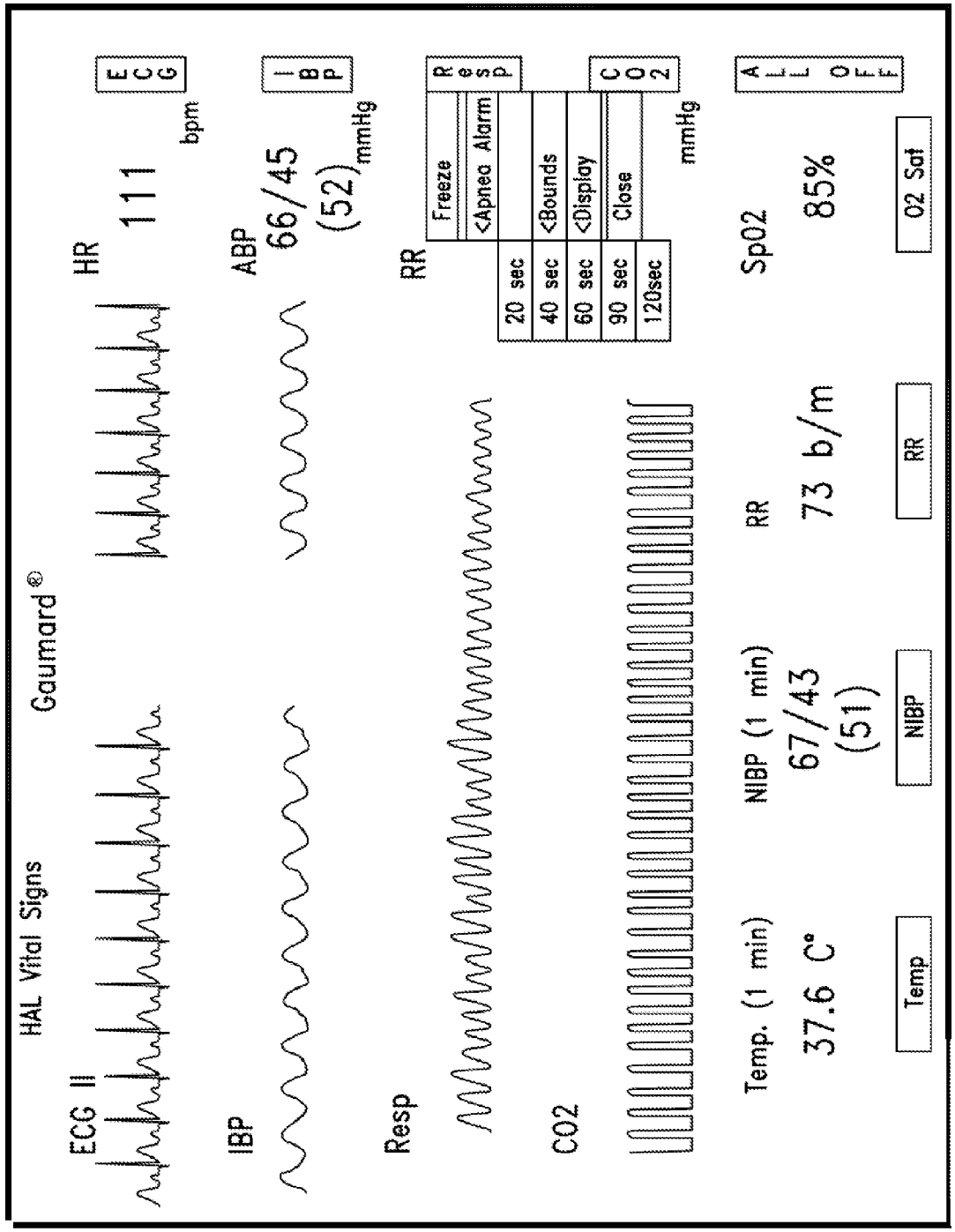
FIG. 23 is an output display view of simulated vital signs of the neonatal simulator of FIG. 17 according to one embodiment of the present disclosure.
Figure 24:
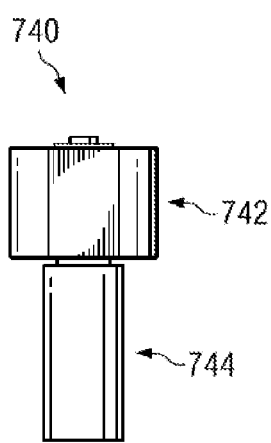
FIG. 24 is a front view of a mechanism for securing the fetal/neonatal simulator to the maternal simulator according to one embodiment of the present disclosure.

In one embodiment, the instructor can select the degree of cyanosis of the neonatal simulator 600, as shown in the screen display 700 of FIG. 22. Though not shown in the screen display 700, the instructor may also select or define various other attributes of the neonatal simulator 600, such as the muscle tone in the arms 622, 624 and the legs 626, 628 (e.g., limp, well-flexed, motion, etc.) and the "speech" of the neonatal simulator 600 (e.g., crying, grunting, stridor, etc.). The vital signs and recovery of the neonatal simulator 600 can be monitored using a display 702, as shown in FIG. 23. The program also provides for an override if coloration changes are not desired.

Referring now to FIGS. 24-27, shown therein is an engagement system 740 that is an alternative embodiment to the receiver 342 and projection 344 system for selectively engaging the fetal or neonatal simulator 302, 600 to the maternal simulator 300. The engagement system 740 includes a mechanism 742 that engages a mechanism 744. In some embodiments, the mechanism 742 is disposed within the fetal or neonatal simulator 302, 600 and the mechanism 744 is disposed within the maternal simulator 300. In one embodiment, the mechanism 742 is adapted to replace the receiver 342 and the mechanism 744 is adapted to replace the projection 744. In other embodiments, the mechanism 742 is disposed within the maternal simulator 300 and the mechanism 744 is disposed within the fetal or neonatal simulator 302, 600.

Figure 25:
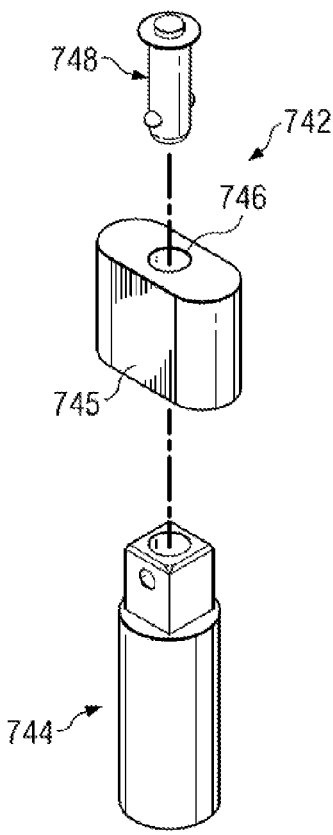
FIG. 25 is a perspective, exploded view of the mechanism of FIG. 24.

Referring more specifically to FIG. 25, the mechanism 742 includes a housing 745 with a opening 746 extending therethrough. In the current embodiment the opening 746 is centrally located and substantially cylindrical. In other embodiments, the opening 746 can have various other cross-sectional shapes, including polygon, irregular, and other shapes. The mechanism 742 also includes a locking portion 748. The locking portion 748 and housing 745 can be permanently secured together (e.g. glued) or temporarily secured together (e.g. threaded engagement). Further, the locking portion 748 and/or the housing 745 may include additional features not shown to facilitate the engagement between the two pieces. In other embodiments the housing 745 and the locking portion 748 are an integral piece.

Figure 26:
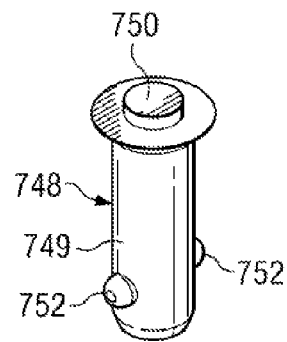
FIG. 26 is a perspective view of a portion of the mechanism of FIG. 24.

As shown in FIG. 26, the locking portion 748 includes a body portion 749. The body portion 749 is adapted to mate with the opening 746 of the mechanism 742. Thus, in the current embodiment the body portion 749 is substantially cylindrical, but in other embodiments may have other cross-sectional shapes to match opening 746. The locking portion 748 further includes an actuator 750 for moving locking pins 752 from an extended position, shown in FIG. 26, to a retracted position. In one embodiment the retracted position of the locking pins 752 is substantially within the body portion 749 of the locking portion. As described below, the selective extension and retraction of the locking pins 752 causes selective engagement of the mechanism 742 with the mechanism 744. In this manner the fetal and neonatal simulators 302, 600 are selectively engaged with the maternal simulator 300. In some embodiments, the actuator 750 is selective actuated by a solenoid. In some embodiments, the solenoid is disposed within the fetal or neonatal simulator 302, 600 or maternal simulator 300 adjacent the actuator 150. In some embodiments, the solenoid is located within the mechanism 742. In some embodiments, the solenoid is actuated via wireless device or a computer system such that an instructor can selectively release the fetal or neonatal simulator.

Figure 27:
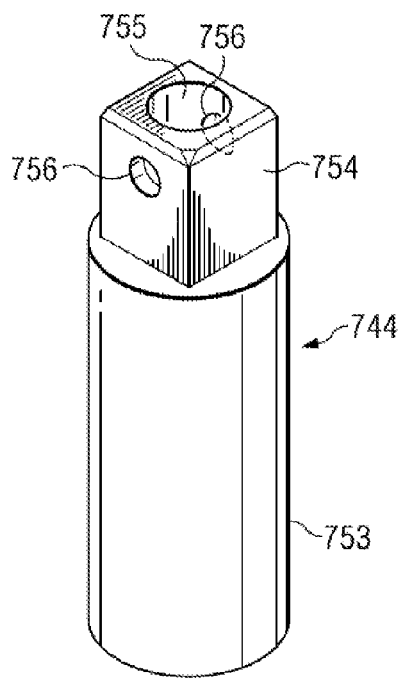
FIG. 27 is a perspective view of another portion of the mechanism of FIG. 24.

Referring more specifically to FIG. 27, the mechanism 744 includes a body portion 754. In the current embodiment, the body portion 753 is substantially cylindrical, but in other embodiments has other cross-sectional shapes. The mechanism 744 also includes an engagement portion 754. The engagement portion 754 has a substantially square cross-sectional shape, but in other embodiments has other cross-sectional shapes. The engagement portion 754 further includes an opening 755 extending therethrough. The opening 755 is adapted to receive the locking portion 748 of the mechanism 742. The engagement portion 754 also includes locking openings 756. The locking pins 752 of the locking portion 748 are adapted to engage openings 756 when extended. When retracted, the locking pins 752 retract from the openings 756 releasing locking mechanism 748 from the engagement portion 754.

Figure 28:
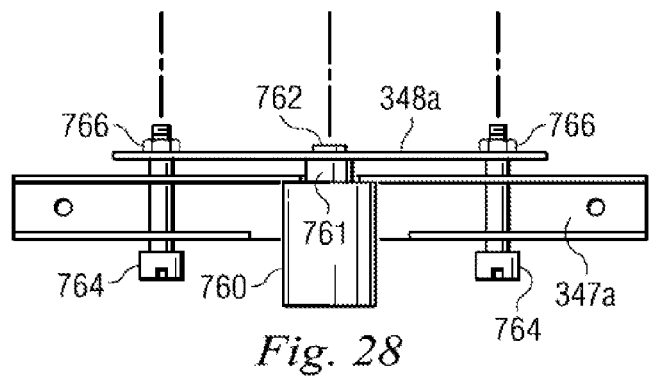
FIG. 28 is a side view of a system for causing selective rotation of the fetal/neonatal simulator during a birthing simulation.

Referring to FIG. 28, shown therein is a system for providing selective rotation to the fetal or neonatal simulators 302, 600. The system is adapted to move the cam 348a between a first position for causing rotation of the fetal simulator and a second position that does not cause rotation of the fetal simulator. In this manner the system can be used to selectively rotate or not rotate the fetal simulator during a birthing simulation. In some embodiments, retracting the cam 348a to a position adjacent the track 347a prevents rotation of the fetal simulator. In some embodiments, the cam 348a is further moveable to an intermediate position that causes some rotation of the fetal simulator, but less rotation than the first position. In some embodiments, the cam 348a is moveable between a plurality of intermediate positions each allowing a different amount of rotational movement. In some embodiments, the plurality of intermediate positions and the amount of rotation are continuous. In other embodiments, the plurality of intermediate positions and the amount of rotation are discrete.

The system includes a solenoid 760 that is adapted to selectively retract the cam 348a. The solenoid 760 is a connected to the cam 348a via an extension 761 and a fixation member 762. In one embodiment, the fixation member 762 is a bolt, screw, other threaded member, or other device for connecting the cam 348a to the extension 761. The cam 348a is connected to track 347a via fixation members 764 and 766. The fixation members 764 and 766 in some embodiments are bolts and nuts. The fixation members 764 and 766 also serve to prevent unwanted translational and rotational movement of the cam 348a with respect to track 347a. In other embodiments, the cam 348a and solenoid 760 may be adapted to translate along the track 347a. Further, in some embodiments the cam 348a may be adapted for rotational movement with respect to track 347a. In some embodiments, the position of the cam 348a is controlled remotely, and in some embodiments wirelessly, by the instructor or computer program. Though the system has been described with respect to track 347a and cam 348a, the same system is applied to track 347b and 348b.

Although illustrative embodiments have been shown and described, a wide range of modification, change, and substitution is contemplated in the foregoing disclosure and in some instances, some features of the present embodiment may be employed without a corresponding use of the other features. It is understood that several variations may be made in the foregoing without departing from the scope of the embodiment. For example, the system 10 may be modified by simply modifying the program 15a and/or the virtual instruments 30 and sensors 30. Accordingly, it is appropriate that the appended claims be construed broadly and in a manner consistent with the scope of the embodiment.

What is claimed is:

1. A maternal simulator for teaching patient care to a user, the maternal simulator comprising:
    a body sized and shaped to simulate a pregnant woman;
    a birthing device positioned within a cavity of the body, the birthing device configured to interface with a fetal simulator and configured to translate and rotate the fetal simulator in a manner simulating a birthing sequence; and
    a distensible cervix coupled to the body, the distensible cervix defining a port that the fetal simulator moves through during the birthing sequence.

2. The maternal simulator of claim 1, wherein the port has a variable diameter.

3. The maternal simulator of claim 2, wherein the variable diameter of the port expands to approximately 10 cm during the birthing sequence.

4. The maternal simulator of claim 2, wherein the variable diameter of the port changes based on a relative position of the fetal simulator.

5. The maternal simulator of claim 1, further comprising a placenta disposed within the maternal simulator.

6. The maternal simulator of claim 1, further comprising simulated circulatory components.

7. The maternal simulator of claim 6, wherein the simulated circulatory components include a simulated heart.

8. The maternal simulator of claim 7, wherein a beat of the simulated heart is generated by a pulsatile flow.

9. The maternal simulator of claim 7, wherein a beat of the simulated heart is controlled by a software program.

10. The maternal simulator of claim 6, wherein the simulated circulatory components include one or more palpable pulse generators.

11. The maternal simulator of claim 10, wherein the one or more palpable pulse generators are positioned at one or more of a carotid location, a brachial location, a radial location, a femoral location, or a pedis dorsis location.

12. The maternal simulator of claim 1, further comprising simulated respiratory components.

13. The maternal simulator of claim 12, wherein the simulated respiratory components include at least one simulated lung.

14. The maternal simulator of claim 12, wherein the simulated respiratory components include an airway.

15. The maternal simulator of claim 14, wherein a resistance of the airway is adjustable.

16. The maternal simulator of claim 15, wherein the resistance of the airway is controlled by a software program.

17. The maternal simulator of claim 1, wherein interaction of a first component of the birthing device with a second component of the birthing device causes the fetal simulator to rotate.

18. The maternal simulator of claim 17, wherein the first component includes a projection.

19. The maternal simulator of claim 18, wherein the second component includes a track.

20. The maternal simulator of claim 18, wherein the second component includes a cam.

* * * * *